(12) United States Patent
Berestka et al.

(10) Patent No.: US 10,092,183 B2
(45) Date of Patent: Oct. 9, 2018

(54) SYSTEMS AND METHODS FOR ANALYZING THE EYE

(71) Applicant: John Berestka, Minneapolis, MN (US)

(72) Inventors: John Berestka, Minneapolis, MN (US); Noah John Berestka, Minneapolis, MN (US)

(73) Assignee: Dr. John Berestka, Minneapolis, MN (US)

( * ) Notice: Subject to any disclaimer, the term of this patent is extended or adjusted under 35 U.S.C. 154(b) by 0 days.

(21) Appl. No.: 15/438,480

(22) Filed: Feb. 21, 2017

(65) Prior Publication Data

US 2017/0156591 A1    Jun. 8, 2017

Related U.S. Application Data

(63) Continuation-in-part of application No. PCT/US2015/047747, filed on Aug. 31, 2015.

(60) Provisional application No. 62/044,253, filed on Aug. 31, 2014.

(51) Int. Cl.
| | | |
|---|---|---|
| A61B 3/14 | (2006.01) | |
| A61B 3/10 | (2006.01) | |
| A61B 3/02 | (2006.01) | |
| A61B 3/135 | (2006.01) | |
| A61B 3/00 | (2006.01) | |
| A61B 8/10 | (2006.01) | |

(52) U.S. Cl.
CPC ............ *A61B 3/135* (2013.01); *A61B 3/0025* (2013.01); *A61B 3/0041* (2013.01); *A61B 3/0083* (2013.01); *A61B 3/14* (2013.01); *A61B 8/10* (2013.01)

(58) Field of Classification Search
CPC ........... A61B 3/14; A61B 3/0025; A61B 3/12; A61B 3/102; A61B 3/0058
USPC .................................................. 351/200–246
See application file for complete search history.

(56) References Cited

U.S. PATENT DOCUMENTS

| | | |
|---|---|---|
| 725,567 A | 4/1903 | Ives |
| 2,039,648 A | 5/1936 | Ives |
| 2,427,689 A | 9/1947 | Osterberg et al. |
| 3,948,585 A | 4/1976 | Heine et al. |
| 3,971,065 A | 7/1976 | Bayer |
| 3,985,419 A | 10/1976 | Matsumoto et al. |
| 4,099,051 A | 7/1978 | Gugliotta |
| 4,180,313 A | 12/1979 | Inuiya |
| 4,193,093 A | 3/1980 | St. Clair |
| 4,230,942 A | 10/1980 | Stauffer |

(Continued)

FOREIGN PATENT DOCUMENTS

| | | |
|---|---|---|
| CN | 102871643 | 1/2013 |
| EP | 2695572 A1 | 2/2014 |
| WO | WO 2013/162471 A2 | 10/2013 |

OTHER PUBLICATIONS

International Search Report and Written Opinion of the International Searching Authority, PCT/US2015/047747, dated Jan. 20, 2016, 13 pages.

(Continued)

*Primary Examiner* — Mohammed Hasan
(74) *Attorney, Agent, or Firm* — Faegre Baker Daniels LLP

(57) ABSTRACT

Systems and methods for imaging an eye are disclosed. The systems and methods may include at least one plenoptic camera. The systems and methods may include an illumination source with a plurality of lights.

17 Claims, 31 Drawing Sheets

(56) References Cited

U.S. PATENT DOCUMENTS

| | | |
|---|---|---|
| 4,370,033 A | 1/1983 | Kani et al. |
| 4,383,170 A | 5/1983 | Takagi et al. |
| 4,422,736 A | 12/1983 | Nunokawa |
| 4,477,159 A | 10/1984 | Mizuno et al. |
| 4,580,219 A | 4/1986 | Pelc et al. |
| 4,642,678 A | 2/1987 | Cok |
| 4,661,986 A | 4/1987 | Adelson |
| 4,694,185 A | 9/1987 | Weiss |
| 4,715,704 A | 12/1987 | Biber et al. |
| 4,732,453 A | 3/1988 | deMontebello et al. |
| 4,774,574 A | 9/1988 | Daly et al. |
| 4,812,643 A | 3/1989 | Talbot |
| 4,838,678 A | 6/1989 | Hubertus |
| 4,844,617 A | 7/1989 | Kelderman et al. |
| 4,849,782 A | 7/1989 | Koyama et al. |
| 4,920,419 A | 4/1990 | Easterly |
| 5,000,563 A | 3/1991 | Gisel et al. |
| 5,076,687 A | 12/1991 | Adelson |
| 5,099,354 A | 3/1992 | Lichtman et al. |
| 5,189,511 A | 2/1993 | Parulski et al. |
| 5,220,360 A | 6/1993 | Verdooner et al. |
| 5,248,876 A | 9/1993 | Kerstens et al. |
| 5,270,747 A | 12/1993 | Kitajima et al. |
| 5,282,045 A | 1/1994 | Mimura et al. |
| 5,321,446 A | 6/1994 | Massig et al. |
| 5,349,398 A | 9/1994 | Koester |
| 5,361,127 A | 11/1994 | Daily |
| 5,387,952 A | 2/1995 | Byer |
| 5,394,205 A | 2/1995 | Ochiai et al. |
| 5,400,093 A | 3/1995 | Timmers |
| 5,436,679 A | 7/1995 | Ohtsuka et al. |
| 5,446,276 A | 8/1995 | Iyoda et al. |
| 5,493,335 A | 2/1996 | Parulski et al. |
| 5,652,621 A | 7/1997 | Adams, Jr. et al. |
| 5,659,390 A | 8/1997 | Danko |
| 5,659,420 A | 8/1997 | Wakai et al. |
| 5,668,597 A | 9/1997 | Parulski et al. |
| 5,717,480 A | 2/1998 | Brooks et al. |
| 5,729,011 A | 3/1998 | Sekiguchi |
| 5,748,371 A | 5/1998 | Cathey, Jr. et al. |
| 5,757,423 A | 5/1998 | Tanaka et al. |
| 5,763,871 A | 6/1998 | Ortyn et al. |
| 5,793,379 A | 8/1998 | Lapidous |
| 5,883,695 A | 3/1999 | Paul |
| 5,912,699 A | 6/1999 | Hayenga et al. |
| 5,946,077 A | 8/1999 | Nemirovskiy |
| 5,949,433 A | 9/1999 | Klotz |
| 5,993,001 A | 11/1999 | Bursell et al. |
| 6,023,523 A | 2/2000 | Cohen et al. |
| 6,028,606 A | 2/2000 | Kolb et al. |
| 6,072,623 A | 6/2000 | Kitajima et al. |
| 6,091,075 A | 7/2000 | Shibata et al. |
| 6,097,394 A | 8/2000 | Levoy et al. |
| 6,097,541 A | 8/2000 | Davies et al. |
| 6,137,535 A | 10/2000 | Meyers |
| 6,137,937 A | 10/2000 | Okano et al. |
| 6,192,162 B1 | 2/2001 | Hamilton, Jr. et al. |
| 6,201,619 B1 | 3/2001 | Neale et al. |
| 6,201,899 B1 | 3/2001 | Bergen |
| 6,268,846 B1 | 7/2001 | Georgiev |
| 6,283,596 B1 | 9/2001 | Yoshimura et al. |
| 6,292,218 B1 | 9/2001 | Parulski et al. |
| 6,301,416 B1 | 10/2001 | Okano et al. |
| 6,320,979 B1 | 11/2001 | Melen |
| 6,339,506 B1 | 1/2002 | Wakelin et al. |
| 6,351,269 B1 | 2/2002 | Georgiev |
| 6,476,805 B1 | 11/2002 | Shum et al. |
| 6,483,535 B1 | 11/2002 | Tamburrino et al. |
| 6,538,249 B1 | 3/2003 | Takane et al. |
| 6,575,575 B2 | 6/2003 | O'Brien et al. |
| 6,577,342 B1 | 6/2003 | Wester |
| 6,580,502 B1 | 6/2003 | Kuwabara |
| 6,597,859 B1 | 7/2003 | Leinhart et al. |
| 6,711,283 B1 | 3/2004 | Soenksen |
| 6,715,878 B1 | 4/2004 | Gobbi et al. |
| 6,738,533 B1 | 5/2004 | Shum et al. |
| 6,838,650 B1 | 1/2005 | Toh |
| 6,842,297 B2 | 1/2005 | Dowski, Jr. |
| 6,875,973 B2 | 4/2005 | Ortyn et al. |
| 6,900,841 B1 | 5/2005 | Mihara |
| 6,927,922 B2 | 8/2005 | George et al. |
| 6,934,056 B2 | 8/2005 | Gindele et al. |
| 7,015,418 B2 | 3/2006 | Cahill et al. |
| 7,019,671 B2 | 3/2006 | Kawai |
| 7,034,866 B1 | 4/2006 | Colmenarez et al. |
| 7,054,067 B2 | 5/2006 | Okano et al. |
| 7,085,062 B2 | 8/2006 | Hauschild |
| 7,109,459 B2 | 9/2006 | Kam et al. |
| 7,118,217 B2 | 10/2006 | Kardon et al. |
| 7,156,518 B2 | 1/2007 | Cornsweet et al. |
| 7,336,430 B2 | 2/2008 | George et al. |
| 7,338,167 B2 | 3/2008 | Zelvin et al. |
| 7,377,644 B2 | 5/2008 | Davis |
| 7,425,067 B2 | 9/2008 | Warden et al. |
| 7,485,834 B2 | 2/2009 | Gouch |
| 7,542,077 B2 | 6/2009 | Miki |
| 7,549,748 B2 | 6/2009 | Davis |
| 7,620,309 B2 | 11/2009 | Georgiev |
| 7,623,726 B1 | 11/2009 | Georgiev |
| 7,706,632 B2 | 4/2010 | Gouch |
| 7,723,662 B2 | 5/2010 | Levoy et al. |
| 7,732,744 B2 | 6/2010 | Utagawa |
| 7,744,219 B2 | 6/2010 | Davis |
| 7,792,423 B2 | 9/2010 | Raskar et al. |
| 7,847,837 B2 | 12/2010 | Ootsuna et al. |
| 7,854,510 B2 | 12/2010 | Verdooner et al. |
| 7,880,794 B2 | 2/2011 | Yamagata et al. |
| 7,936,392 B2 | 5/2011 | Ng et al. |
| 7,949,252 B1 | 5/2011 | Georgiev |
| 7,956,924 B2 | 6/2011 | Georgiev |
| 7,965,936 B2 | 6/2011 | Raskar et al. |
| 8,019,215 B2 | 9/2011 | Georgiev et al. |
| 8,228,417 B1 | 7/2012 | Georgiev et al. |
| 8,238,738 B2 | 8/2012 | Georgiev |
| 8,289,440 B2 | 10/2012 | Knight et al. |
| 8,434,869 B2 | 5/2013 | Davis |
| 8,471,897 B2 | 6/2013 | Rodriguez Ramos et al. |
| 8,593,564 B2 | 11/2013 | Border et al. |
| 8,619,177 B2 | 12/2013 | Perwass et al. |
| 2001/0012149 A1 | 8/2001 | Lin et al. |
| 2001/0050813 A1 | 12/2001 | Allio |
| 2002/0140835 A1 | 10/2002 | Silverstein |
| 2002/0159030 A1 | 10/2002 | Frey et al. |
| 2003/0020883 A1 | 1/2003 | Hara |
| 2003/0067596 A1 | 4/2003 | Leonard |
| 2003/0103670 A1 | 6/2003 | Schoelkopf et al. |
| 2003/0117511 A1 | 6/2003 | Belz et al. |
| 2003/0156077 A1 | 8/2003 | Balogh |
| 2003/0160957 A1 | 8/2003 | Oldham et al. |
| 2003/0231255 A1 | 12/2003 | Szajewski et al. |
| 2004/0114176 A1 | 6/2004 | Bodin et al. |
| 2004/0114807 A1 | 6/2004 | Lelescu et al. |
| 2004/0223214 A1 | 11/2004 | Atkinson |
| 2004/0256538 A1 | 12/2004 | Olson et al. |
| 2004/0257360 A1 | 12/2004 | Sieckmann |
| 2005/0080602 A1 | 4/2005 | Snyder et al. |
| 2005/0088714 A1 | 4/2005 | Kremen |
| 2005/0122418 A1 | 6/2005 | Okita et al. |
| 2005/0286019 A1 | 12/2005 | Wiltberger et al. |
| 2005/0286800 A1 | 12/2005 | Gouch |
| 2006/0050229 A1 | 3/2006 | Farberov |
| 2006/0104542 A1 | 5/2006 | Blake et al. |
| 2006/0176566 A1 | 8/2006 | Boettiger et al. |
| 2006/0238847 A1 | 10/2006 | Gouch |
| 2007/0024931 A1 | 2/2007 | Compton et al. |
| 2007/0036462 A1 | 2/2007 | Crandall et al. |
| 2007/0046862 A1 | 3/2007 | Umebayashi et al. |
| 2007/0071316 A1 | 3/2007 | Kubo |
| 2007/0091197 A1 | 4/2007 | Okayama et al. |
| 2007/0147673 A1 | 6/2007 | Crandall |
| 2007/0230944 A1 | 10/2007 | Georgiev |
| 2007/0252074 A1 | 11/2007 | Ng et al. |
| 2007/0257772 A1 | 11/2007 | Marcelle et al. |
| 2008/0007626 A1 | 1/2008 | Wernersson |

(56) References Cited

U.S. PATENT DOCUMENTS

| | | |
|---|---|---|
| 2008/0018668 A1 | 1/2008 | Yamauchi |
| 2008/0044063 A1 | 2/2008 | Friedman et al. |
| 2008/0056549 A1 | 3/2008 | Hamill et al. |
| 2008/0107231 A1 | 5/2008 | Miyazaki et al. |
| 2008/0131019 A1 | 6/2008 | Ng |
| 2008/0152215 A1 | 6/2008 | Horie et al. |
| 2008/0165270 A1 | 7/2008 | Watanabe et al. |
| 2008/0166063 A1 | 7/2008 | Zeng |
| 2008/0180792 A1 | 7/2008 | Georgiev |
| 2008/0187305 A1 | 8/2008 | Raskar et al. |
| 2008/0193026 A1 | 8/2008 | Horie et al. |
| 2008/0218610 A1 | 9/2008 | Chapman et al. |
| 2008/0226274 A1 | 9/2008 | Spielberg |
| 2008/0247623 A1 | 10/2008 | Delso et al. |
| 2008/0266655 A1 | 10/2008 | Levoy et al. |
| 2008/0309813 A1 | 12/2008 | Watanabe |
| 2009/0027542 A1 | 1/2009 | Yamamoto et al. |
| 2009/0041381 A1 | 2/2009 | Georgiev et al. |
| 2009/0041448 A1 | 2/2009 | Georgiev et al. |
| 2009/0086304 A1 | 4/2009 | Yurlov et al. |
| 2009/0102956 A1 | 4/2009 | Georgiev |
| 2009/0128658 A1 | 5/2009 | Hayasaka et al. |
| 2009/0128669 A1 | 5/2009 | Ng et al. |
| 2009/0140131 A1 | 6/2009 | Utagawa |
| 2009/0185801 A1 | 7/2009 | Georgiev et al. |
| 2009/0200623 A1 | 8/2009 | Qian et al. |
| 2009/0225279 A1 | 9/2009 | Small |
| 2009/0268970 A1 | 10/2009 | Babacan et al. |
| 2009/0273843 A1 | 11/2009 | Raskar et al. |
| 2009/0295829 A1 | 12/2009 | Georgiev et al. |
| 2010/0026852 A1 | 2/2010 | Ng et al. |
| 2010/0085468 A1 | 4/2010 | Park et al. |
| 2010/0128145 A1 | 5/2010 | Pitts et al. |
| 2010/0129048 A1 | 5/2010 | Pitts et al. |
| 2010/0205388 A1 | 8/2010 | MacInnis |
| 2010/0265386 A1 | 10/2010 | Raskar et al. |
| 2011/0169994 A1 | 7/2011 | DeFrancesco et al. |
| 2011/0234841 A1 | 9/2011 | Akeley et al. |
| 2011/0234977 A1 | 9/2011 | Verdooner |
| 2011/0273609 A1 | 11/2011 | DeFrancesco et al. |
| 2011/0313294 A1* | 12/2011 | de Roode ............ A61B 5/0059 600/473 |
| 2012/0101371 A1 | 4/2012 | Verdooner |
| 2012/0249550 A1 | 10/2012 | Akeley et al. |
| 2012/0294590 A1 | 11/2012 | Pitts et al. |
| 2012/0327222 A1 | 12/2012 | Ng et al. |
| 2013/0010260 A1 | 1/2013 | Tumlinson et al. |
| 2013/0033636 A1 | 2/2013 | Pitts et al. |
| 2013/0113981 A1 | 5/2013 | Knight et al. |
| 2013/0169934 A1 | 7/2013 | Verdooner |
| 2013/0208241 A1 | 8/2013 | Lawson et al. |
| 2013/0222606 A1 | 8/2013 | Pitts et al. |
| 2013/0222633 A1 | 8/2013 | Knight et al. |
| 2013/0222652 A1 | 8/2013 | Akeley et al. |
| 2013/0235267 A1 | 9/2013 | Pitts et al. |
| 2013/0301003 A1* | 11/2013 | Wells ................... A61B 3/0091 351/206 |
| 2014/0013273 A1 | 1/2014 | Ng |
| 2014/0016019 A1 | 1/2014 | Pitts et al. |
| 2014/0078259 A1 | 3/2014 | Hiramoto et al. |
| 2014/0129988 A1 | 5/2014 | Liang et al. |
| 2014/0218685 A1* | 8/2014 | Nakamura ........... A61B 3/0091 351/206 |
| 2014/0300817 A1* | 10/2014 | Bezman ................ H04N 5/91 348/616 |

OTHER PUBLICATIONS

Wilburn, Bennett et al., *High Performance Imaging Using Large Camera Arrays*, ACM Transactions on Graphics (proceedings SIGGRAPH) vol. 24, No. 3., 2005, pp. 765-776.

Veeraraghavan, Ashok et al., *Dappled Photography: Mask Enhanced Cameras for Heterodyned Light Fields and Coded Aperture Refocusing*, Mitsubishi Electric Research Laboratories, Proc. ACM SIGGRAPH, Jul. 2007, http://www.merl.com, 12 pages.

Raskar, Ramesh et al., *Glare Aware Photography: 4D Ray Sampling for Reducing Glare Effects of Camera Lenses*, Mitsubishi Electric Research Laboratories, SIGGRAPH 2008, http://www.merl.com, 12 pages.

Manakov, Alkhazur et al., *A Reconfigurable Camera Add-On for High Dynamic Range, Multispectral, Polarization, and Light-Field Imaging*, ACM Transactions on Graphics, Association for Computing Machinery, 2013, Proceeding of SIGGRAPH, 32 (4), pp. 47:1-47-14.

* cited by examiner

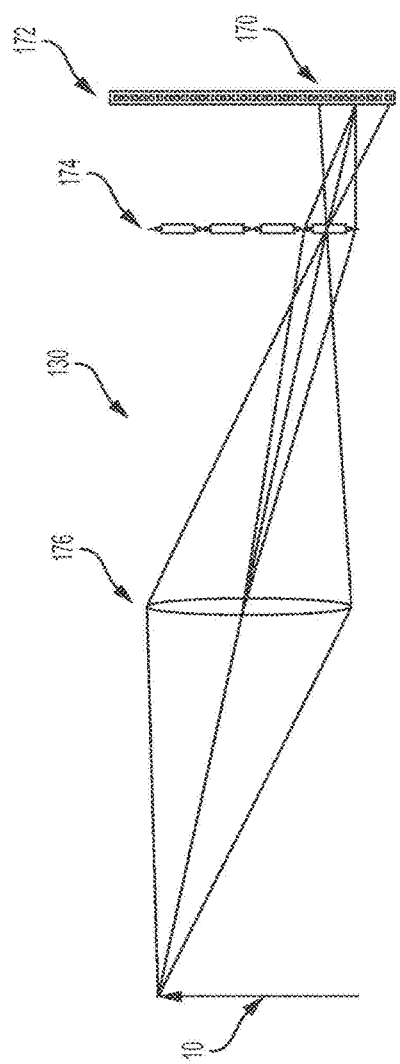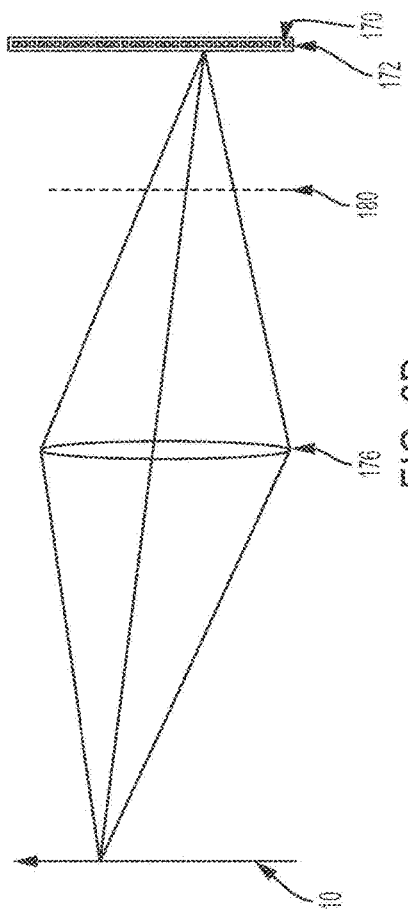
FIG. 2A
FIG. 2B

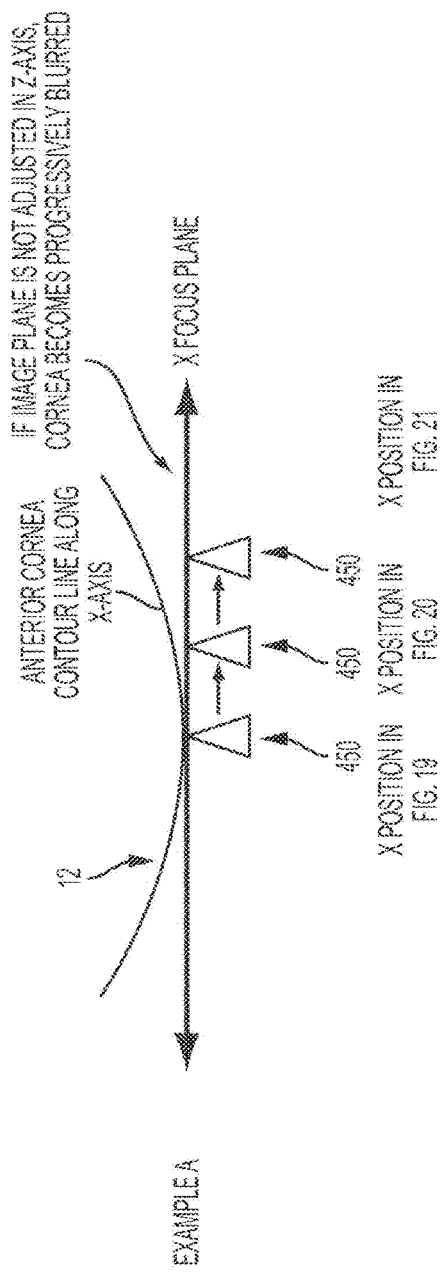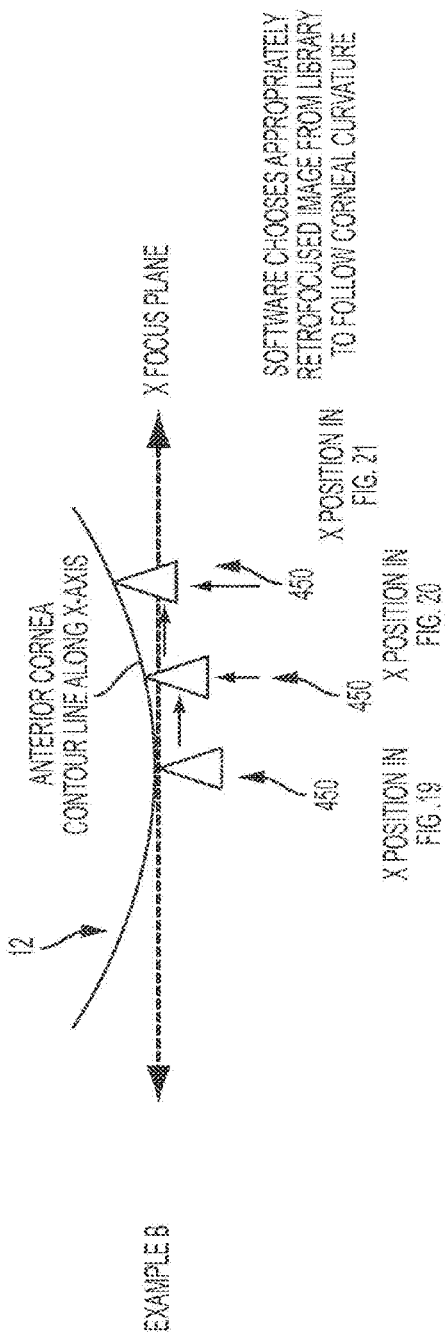
FIG. 24B
FIG. 24C

SYSTEMS AND METHODS FOR ANALYZING THE EYE

RELATED APPLICATIONS

This application is a continuation-in-part of PCT Application Ser. No. PCT/US2015/047747, filed Aug. 31, 2015, titled SYSTEMS AND METHODS FOR ANALYZING THE EYE, which claims the benefit of U.S. Provisional Application 62/044,253, filed Aug. 31, 2014, titled SYSTEMS AND METHODS FOR ANALYZING THE EYE, the entire disclosures of which are expressly incorporated by reference herein.

TECHNICAL FIELD

The present invention relates to one or more imaging systems including at least one light source, optics, and at least one camera for capturing and recording images of a patient's eye. The invention further relates to a system and methods for allowing an ophthalmologist to easily and conveniently recreate the slit-lamp examination by accessing the captured images.

BACKGROUND

Ophthalmologists use a variety of devices for imaging of a patient's eye, including slit-lamps, ophthalmoscopes, fundus cameras, and scanning laser ophthalmoscopes (SLOs). The ophthalmic slit-lamp examination has remained largely unchanged for over sixty years. The slit lamp is a versatile instrument used by ophthalmologists for examining a patient's eye. It consists of a microscope, an illumination source, and a mechanical support system to facilitate positioning the illumination source at various angles with respect to the eye. Ophthalmologists and optometrists typically examine the eye by first horizontally scanning across the eye using various slit beam thicknesses and orientations to examine the most anterior structures such as the cornea and conjunctiva. Then the examiner will adjust the focus plane posterior to horizontally scan across the anterior chamber of the eye. The focus is then adjusted more posteriorly to horizontally scan across the iris and anterior crystalline lens. The process is repeated again to examine the posterior aspect of the crystalline lens and anterior vitreous.

FIG. 1 shows a schematic view of a patient's eye. As shown in FIG. 1, the basic components of the eye 10 include a cornea 12, conjunctiva 14, an iris 16, a pupil 18, a crystalline lens 20, and a retina 22. An anterior chamber 24 is provided behind the cornea 12. A posterior chamber 40 is provided posterior of anterior chamber 24. The posterior chamber 40 includes the lens 20 which is positioned by the suspensory ligaments 34 of the eye. An anterior capsule 31 separates the anterior chamber 24 from a posterior chamber 40 and a posterior capsule 30 separates the posterior chamber 40 from a chamber 32 which includes the vitreous humor. Light enters the front of the eye through the pupil 18, is focused and inverted by the cornea and lens 20, and is projected onto the retina 22 at the back of the eye. The iris 16 functions as an "aperture" that opens and closes to regulate the amount of light entering the eye. The cornea, iris, pupil and lens are often referred to as the anterior segment of the eye. The retina 22 is a multi-layered structure that converts received light into a neural signal through a process known as "signal transduction." The photoreceptors on the retina are known as rods and cones. These generate neural signals that are communicated to the brain by ganglion cells that form the optic nerve 24.

Anterior segment ocular imaging (e.g., slit-lamp) photography allows ophthalmologists to document and record a given slit-lamp view of an eye. Similarly, slit-lamp video allows ophthalmologists to document and record a slit-lamp examination of a patient's eye. Traditional slit-lamp photography creates an image using a sensor placed in an optical system at a plane optically conjugate to an object which is to be imaged. This is the plane at which the best focus is achieved and therefore the best optical resolution of features in the object results.

Most still and video photography slit-lamp units are created by mounting a camera in place of the viewing oculars or in conjunction with the viewing oculars through the means of a beam splitter. These traditional modalities of recording the slit-lamp exam are limited to either using still photography to capture a single moment of the examination, or taking a video of one's own examination sequence of slit-beam focus, magnification, slit-beam height, width and angle of incidence. Another health care professional can view the video, but cannot alter any of these variables after the examination. Slit-lamp video also requires a highly trained ophthalmologist or optometrist to perform the examination. No system exists that allows an ophthalmologist or optometrist to perform a virtual slit-lamp examination based on images obtained at an earlier time. Such a system using traditional cameras would require a massive library of images of various slit-beam positions and characteristics would be required, with numerous sequential images stored in at least the x- and z-axes.

A camera captures an image of the illuminated portion of the eye structures via reflected light. Rays which emanate from a point within the object plane in multiple directions are captured by the optical system and those rays converge to approximately a single point in the conjugate image plane. The set of rays which are summed at any image point is generally constrained by physical apertures placed within the optical assembly. The traditional sensor records the summation of the intensity of light in the plane of the detector. The measurement contains the intensity distribution of light within the plane of the sensor but loses all information about the rays' direction before the summation. Therefore the typical process of recording a traditional image does not record a very large fraction of the information contained in the light absorbed.

SUMMARY

In an exemplary embodiment of the present disclosure, an imaging system for imaging at least a portion of an eye of a patient is provided. The system comprising a patient support adapted to position the eye of the patient; a movable base moveable relative to the patient support; and an illumination system. The illumination system including at least one light source producing light to illuminate the eye and an illumination system support arm supporting the light source. The illumination system support arm being supported by the moveable base and rotatable relative to the moveable base. The system further comprising an observation system including a plenoptic camera configured to receive imaging rays produced by reflection of light from the eye, and an observation system support arm supporting the imaging system. The observation system support arm being supported by the moveable base and rotatable relative to the moveable base. The observation system further comprising a storage device operatively coupled to the plenoptic camera to receive and store a plurality of images of the eye imaged by the plenoptic camera, each of the stored images having at least one associated component characteristic of one of the patient support, the movable base, the illumination system, and the observation system. In one example, the illumination system further includes a slit forming device which receives illuminating light produced by the at least one light source and provides a line of light to illuminate the eye, the illumination system support arm supporting the slit forming device and wherein the plenoptic camera receives imaging rays produced by reflection of the line of light from the eye. In another example, the illumination system includes a plurality of light sources arranged in an array, the plurality of light sources each produce light to illuminate the eye. In a variation thereof, an illumination characteristic of a portion of the plurality of light sources is adjusted through an input device. In a refinement thereof, the illumination characteristic is one of an intensity level and a wavelength spectrum. In another variation thereof, an illumination characteristic of a portion of the plurality of light sources is adjusted through an electronic controller. In a refinement thereof, the illumination characteristic is one of an intensity level and a wavelength spectrum. In a further example, the observation system support arm is rotatable relative to the moveable base independent of the illumination system support arm. In yet a further example, the illumination system support arm is rotatable relative to the moveable base about a first rotation axis and the observation system support arm is rotatable relative to the moveable base about the first rotation axis.

In another exemplary embodiment, a method of analyzing an eye of a patient which has been illuminated with a slit-lamp microscope is provided. The slit-lamp microscope including an illumination system and an observation system. The illumination system including a light source and a slit forming device which provides a line of light to illuminate the eye and the observation system including an imaging system including a plenoptic camera configured to receive imaging rays produced by reflection of the line of light from the eye. The method comprising the steps of storing a plurality of images of the eye imaged by the plenoptic camera while the eye was illuminated with the line of light, each of the stored images having at least one associated slit-lamp microscope characteristic; receiving an image request; and providing a requested image based on at least one of the plurality of images, the image request, and the at least one associated slit-lamp microscope characteristic of the at least one of the plurality of images. In one example, the requested image includes the line of light focused on a first portion of a curved structure. In another example, the method further comprises the steps of receiving an image request for a second image having the line of light focused on a second portion of the curved structure, wherein the line of light is displaced in at least one of an x-axis direction and a y-axis direction and in a z-axis direction; and generating the second image from at least one of the stored images and the light field data of the at least one stored image. In a further example, the method further comprises the step of requesting to walk through the stored images sequentially. In yet a further example, the method further comprises the steps of retrieving an image set from a prior examination; and identifying an image from the prior examination having the same associated slit-lamp microscope characteristic as the requested image. In yet a further example, the associated slit-lamp microscope characteristic is one or more of an x-axis position of a moveable base of the slit-lamp supporting the illumination system and the observation system, a y-axis position of the moveable base, a z-axis position of the moveable base, a rotational position of the illumination system, a rotational position of the observation system, a slit width of the slit-forming device, and a magnification of the observation system. In still yet another example, the method further comprises the steps of receiving an image request for a second image having the line of light focused on at a different depth within the eye than the first image; and generating the second image from at least one of the stored images and the light field data of the at least one stored image.

In yet another exemplary embodiment of the present disclosure, an imaging system for imaging at least a portion of an eye of a patient is provided. The system comprising a patient support adapted to position the eye of the patient; an illumination system including a light source producing light to illuminate the eye; and an observation system including a plurality of cameras in a spaced apart arrangement, each camera positioned to receive imaging rays produced by reflection of light from the eye. In one example, each camera has an optical axis and the plurality of optical axes are parallel. In another example, the plurality of cameras are arranged along a line generally perpendicular to the optical axes of the plurality of cameras. In a further example, each camera has an optical axis and the plurality of optical axes converge towards a common point. In a variation thereof, the plurality of cameras are arranged along an arc. In a refinement thereof, the arc is a circular arc and the common point is a center of the circular arc. In still another example, the plurality of cameras are plenoptic cameras.

In a further exemplary embodiment of the present disclosure, a method of analyzing an eye of a patient is provided. The method comprising the steps of illuminating the eye with an illumination system, the illumination system including a light source and a slit forming device which provides a line of light to illuminate the eye; positioning a first camera relative to the eye to receive imaging rays produced by a reflection of the line of light from the eye; positioning a second camera relative to the eye to receive imaging rays produced by the reflection of the line of the light from the eye; and storing a plurality of images of the eye imaged by the first camera and the second camera while the eye was illuminated with the line of light. In one example, each of the first camera and the second camera have an optical axis which are parallel to each other. In a variation thereof, the first camera and the second camera are arranged along a line generally perpendicular to the optical axes of the first camera and the second camera. In another example, each of the first camera and the second camera have an optical axis that converge towards a common point. In another variation thereof, the first camera and the second camera are arranged along an arc. In a refinement thereof, the arc is a circular arc and the common point is a center of the circular arc. In a further refinement thereof, the plurality of cameras are plenoptic cameras.

In yet a further exemplary embodiment of the present disclosure, an imaging system for imaging at least a portion of an eye of a patient is provided. The system comprising a patient support adapted to position the eye of the patient; an illumination system including a light source producing light to illuminate the eye; and an observation system including imaging optics configured to receive imaging rays produced by reflection of light from the eye which are focused by the imaging optics at a first object plane, a first observation unit including a viewfinder which receives imaging rays from the imaging optics and a second observation unit which receives the imaging rays from the imaging optics, the second observation unit including a plenoptic camera and a display, the second observation unit displaying an image of the eye generated based on the imaging rays, the image of the eye being focused at a second object plane spaced apart from the first object plane. In one example, the imaging system further comprises a beamsplitter, the imaging rays reaching the viewfinder through a first path through the beamsplitter and reaching the plenoptic camera through a second path through the beamsplitter. In another example, the first object plane is offset from the second object plane. In a further example, the illumination system includes a plurality of light sources arranged in an array, the plurality of light sources each produce light to illuminate the eye. In a variation thereof, an illumination characteristic of a portion of the plurality of light sources is adjusted through an input device. In a refinement thereof, the illumination characteristic is one of an intensity level and a wavelength spectrum.

In yet still another exemplary embodiment of the present disclosure, a method of analyzing an eye of a patient is provided. The method comprising the steps of illuminating the eye with an illumination system; receiving with imaging optics imaging rays produced by reflection of light from the eye; directing the imaging rays to a viewfinder; directing the imaging ray to a plenoptic camera; focusing the imaging optics on a first object plane in the eye; and displaying on a display operatively coupled to the plenoptic camera a second object plane in the eye. In one example, the first object plane is offset from the second object plane. In a variation thereof, the first object plane take into account at least one of an optical power of the viewfinder and the optical power of an operator's eyes such that the resultant image viewed by the operator through the viewfinder is focused at the second object plane.

In still a further exemplary embodiment of the present disclosure, an imaging system for imaging at least a portion of a left eye of a patient and at least a portion of a right eye of the patient is provided. The system comprising a patient support adapted to position the left eye and the right eye of the patient; at least one illumination system including at least one light source producing light to illuminate the left eye and the right eye; a first observation system including a first plenoptic camera configured to receive imaging rays produced by reflection of light from the left eye; a second observation system including a second plenoptic camera configured to receive imaging rays produced by reflection of light from the right eye; and a storage device operatively coupled to the first plenoptic camera and to the second plenoptic camera to receive and store a plurality of images of the eye imaged by the first plenoptic camera and the second plenoptic camera. In one example, the at least one illumination system includes a first illumination system including at least a first light source producing light to illuminate the left eye and a second illumination system including at least a second light source producing light to illuminate the right eye.

In a further exemplary embodiment of the present disclosure, a method of analyzing an eye of a patient with an imaging system including an illumination system and an observation system is provided. The illumination system includes a light source. The observation system including an imaging system including a camera configured to receive imaging rays produced by reflection of light from the eye. The method comprising the steps of capturing images of a portion of the eye over time with the camera; monitoring a position of a structure of the eye in the captured images; determining if the structure of the eye is moving towards an unsafe location; and if the structure is moving towards an unsafe location, providing feedback of such movement. In one example, the method further comprises the step of providing a signal to inhibit operation of an instrument which is used to alter a portion of the eye. In a variation thereof, the instrument is an ultrasound probe. In another example, the step providing feedback of such movement includes at least one of providing an audio output, providing a visual output, and providing a tactile output. In a further example, the camera is a plenoptic camera. In a variation thereof, the structure is a posterior capsule of the eye and the step of determining if the structure of the eye is moving towards the unsafe location includes the step of determining if the posterior capsule is moving forward towards the anterior side of the eye. In a refinement thereof, the step of determining if the structure of the eye is moving towards the unsafe location includes the step of determining whether the movement of the structure has exceeded a threshold amount. In yet a further example, the step of determining if the structure of the eye is moving towards the unsafe location includes the step of determining whether the movement of the structure has exceeded a threshold amount.

In a yet further exemplary embodiment of the present disclosure, a method of analyzing an eye of a patient with an imaging system including an illumination system and an observation system is provided. The illumination system includes a light source. The observation system including a camera configured to receive imaging rays produced by reflection of light from the eye. The method comprising the steps of capturing images of a portion of the eye over time with a plenoptic camera; determining positions of one of more structures of the eye from the captured images; and identifying a first intraocular lens from a library of intraocular lenses for placement in the eye based on the determined positions. In one example, the step of identifying the first intraocular lens from the library of intraocular lenses for placement in the eye based on the determined positions includes the step of comparing the determined positions of the one or more structures of the eye with a database of determined positions for historical patients and a rating of the selected intraocular lens for the historical patients. In a variation thereof, the determined positions includes a distance between an anterior capsule of the eye and an posterior capsule of the eye and a position of suspensory ligaments of the eye relative to one of the anterior capsule and the posterior capsule. In a refinement thereof, the database also includes a measure of the final position of a replacement lens of the historical patients and the step of identifying a first intraocular lens identifies the a first lens if the measure has a first value indicating the final position of the lens for a historical patient was as expected and a second lens if the measure has a second value indicating that the final position of the lens for the historical patient was different than expected, the second lens having a different optical power than the first lens.

In still another exemplary embodiment of the present disclosure, an imaging system for imaging at least a portion of an eye of a patient is provided. The system comprising a patient support adapted to position the eye of the patient; an illumination system including a plurality of light sources, each producing light to illuminate the eye; and an observation system including imaging optics configured to receive imaging rays produced by reflection of light from the eye. In one example, the observation system includes a plenoptic camera which receives the imaging rays from the imaging optics. In a variation thereof, the imaging system further comprises a storage device operatively coupled to the plenoptic camera to receive and store a plurality of images of the eye imaged by the plenoptic camera, each of the stored images having at least one associated component characteristic of one of the illumination system and the observation system. In another example, the illumination system further includes a slit forming device which receives illuminating light produced by the at least one light source and provides a line of light to illuminate the eye and wherein the plenoptic camera receives imaging rays produced by reflection of the line of light from the eye. In still another example, the plurality of light sources are arranged in an array. In a variation thereof, an illumination characteristic of a portion of the plurality of light sources is adjusted through an input device. In a refinement thereof, the illumination characteristic is one of an intensity level and a wavelength spectrum. In another variation, an illumination characteristic of a portion of the plurality of light sources is adjusted through an electronic controller. In a refinement thereof, the illumination characteristic is one of an intensity level and a wavelength spectrum.

In still another exemplary embodiment of the present disclosure, a method of analyzing an eye of a patient is provided. The method comprising the steps of illuminating the eye with an illumination system, the illumination system including a plurality of light sources; receiving with imaging optics imaging rays produced by reflection of light from the eye; directing the imaging rays to a camera to capture an image; displaying the image; and adjusting an illumination characteristic of a portion of the plurality of light sources to alter an illumination of a portion of the eye. In one example, the illumination characteristic is one of an intensity level and a wavelength spectrum. In another example, the illumination characteristic is adjusted to reduce glare at the portion of the eye.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A illustrates an exemplary embodiment of a plenoptic camera including a lenticular array of lenses;

FIG. 2B illustrates an exemplary embodiment of a plenoptic camera including a mask;

FIGS. 24A-24E illustrate an example of refocusing with the system of the present disclosure;

Figure 1:
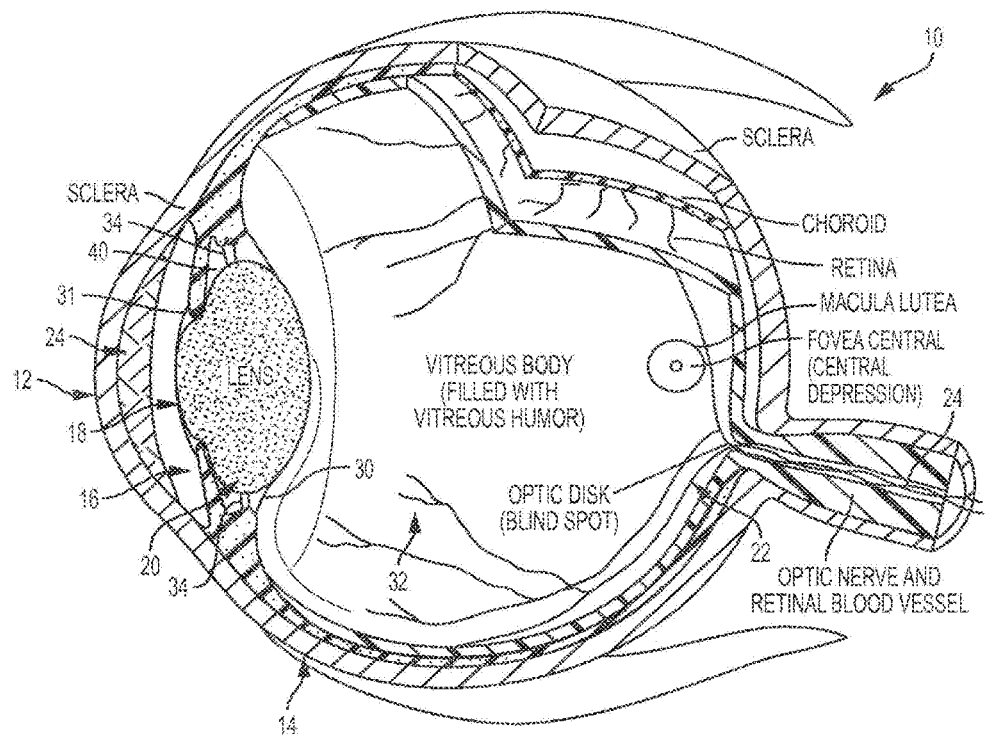
FIG. 1 illustrates a schematic view showing the basic components of the human eye.
Figure 1A:
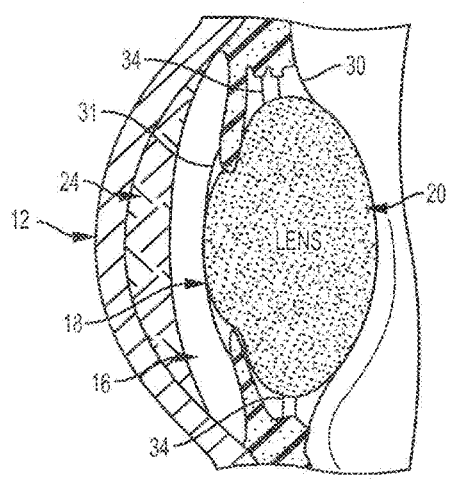
FIG. 1A illustrates an enlarged view of a portion of FIG. 1.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE DRAWINGS

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

Figure 2:
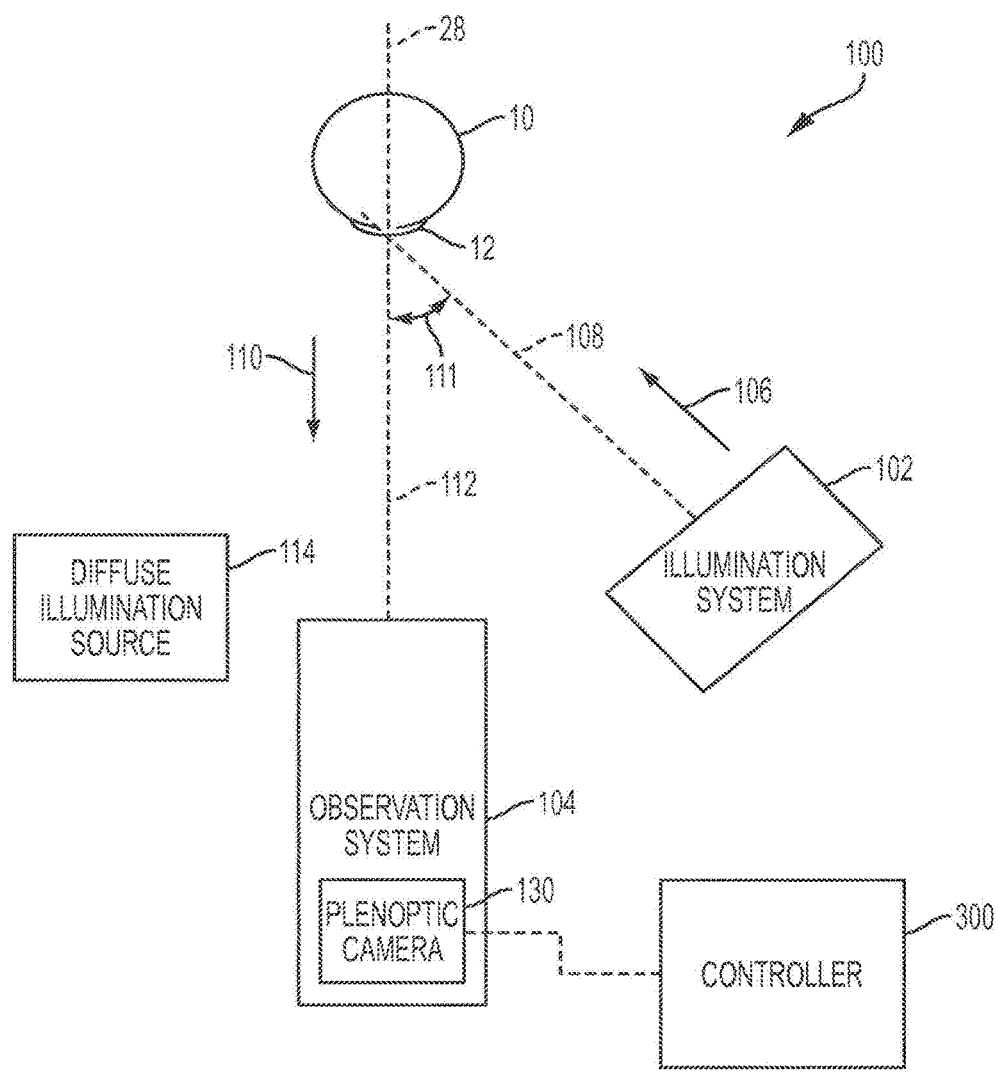
FIG. 2 illustrates an exemplary examination system of the present disclosure with an optical axis of an illumination system being angled relative to an optical axis of an observation system.

Referring to FIG. 2, an examination system 100 is shown. Examination system 100 includes an illumination system 102 and an observation system 104. Illumination system 102 illuminates eye 10 with light generally in direction 106 along an optical axis 108. Observation system 104 receives reflected light from eye 10 generally in direction 110 along an optical axis 112. As shown in FIG. 2, optical axis 112 is generally aligned with an optical axis 28 of eye 10 and optical axis 108 is angled relative to optical axis 112 by an angle 111. In one embodiment, optical axis 108 and optical axis 112 are generally coplanar. Although illumination system 102 and observation system 104 are shown with observation system 104 being positioned directly in front of eye 10 and aligned with axis 28 of the eye 10 and illumination system 102 being angled relative to eye 10, illumination system 102 and observation system 104 may be positioned in any relationship to eye 10. In one embodiment, illumination system 102 and observation system 104 are both angled relative to the optical axis 28 of the eye 10. In one embodiment, illumination system 102 is positioned directly in front of eye 10 with optical axis 108 aligned with optical axis 28 of eye 10 and observation system 104 is positioned with optical axis 112 angled relative to optical axis 28 of the eye 10.

In one embodiment, examination system 100 includes a secondary diffuse illumination source 114 which illuminates portions of the eye not illuminated by the brighter illumination source of illumination system 102. The illumination source 114 may be any light source which provides a generally constant light intensity across a large portion of the eye 10. In one example, secondary diffuse illumination source 114 is supported by illumination system 102. In one example, secondary diffuse illumination source 114 is separate from illumination system 102.

Observation system 104 includes a plenoptic camera 130. Plenoptic camera 130 records light field data associated with the light reflected from eye 10. The light field data permits refocusing of an image recorded by the plenoptic camera 130. Plenoptic camera 130 is operatively coupled to a controller 300. As explained herein, controller 300 stores the images recorded by plenoptic camera 130 and processes image requests. Exemplary plenoptic cameras are the Lytro Illium brand camera available from Lytro, Inc. located at 1300 Terra Bella Avenue in Mountain View, Calif. 94043 and the R5, R11, R29, and RX camera models sold by Raytrix GmbH located at Schauenburgerstrasse 116 D-24118 in Kiel, Germany. Further exemplary plenoptic cameras and/or systems for processing images recorded by plenoptic cameras are disclosed in U.S. Pat. Nos. 7,706,632; 7,936,392; 7,956,924; 8,228,417; 8,238,738; 8,289,440; 8,471,897, 8,593,564; 8,619,177, US20130010260; US20130222633, US20140078259; US20140129988; US20140016019; US20140013273; US20130235267; US20130222652; US20130222606; US20130113981; US20130033636; US20120327222; US20120294590; US20120249550; US20110234841, the disclosures of which are expressly incorporated by reference herein.

Referring to FIG. 2A, in one embodiment, a plenoptic camera 130 includes a sensor array 170 at or near the back focal plane 172 of a lens array (lenticular array) 174. Sensor array 170 includes a plurality of detectors which form pixels in a resultant image. In this way, a ray enters camera 130 passes through a main lens or lenses 176 and then encounters lens array 174. The ray is constrained in position by the individual lens in the array (lenslet) through which it passed, and in angle by the specific sensor pixel it is incident upon behind the lenticular array 174.

Referring to FIG. 2B, in one embodiment, a plenoptic camera 130 includes a sensor array 170 at or near the back focal plane 172 of a mask 180 in place of the lenticular array 174. Sensor array 170 includes a plurality of detectors which form pixels in a resultant image. A ray enters camera 130 passes through a main lens 176 and then encounters mask 180. In one embodiment, the mask 180 is a patterned mask. Additional details regarding an exemplary plenoptic camera that utilizes a mask instead of a lenticular array are provided in (1) Veeraraghavan, A., Raskar, R., Agrawal, A., Mohan, A., Tumblin, J. (2007). "Dappled Photography: Mask Enhanced Cameras for Heterodyned Light Fields and Coded Aperture Refocusing", Proc. ACM SIGGRAPH; (2) Veeraraghavan, A., Raskar, R., Agrawal, A., Mohan, A., Tumblin, J. (July 2007). "Dappled Photography: Mask Enhanced Cameras for Heterodyned Light Fields and Coded Aperture Refocusing", MITSUBISHI ELECTRIC RESEARCH LABORATORIES, http://www.merl.com; and (3) U.S. Pat. No. 7,965,936, titled 4D light field cameras, the disclosures of which are expressly incorporated by reference herein.

An additional exemplary plenoptic camera 130 is disclosed in MANAKOV, Alkhazur et al., A Reconfigurable Camera Add-On for High Dynamic Range, Multispectral, Polarization, and Light-Field Imaging, ACM Transactions on Graphics, Association for Computing Machinery, 2013, Proceeding of SIGGRAPH, 32 (4), pp. 47:1-47-14, the disclosure of which is expressly incorporated by reference herein, wherein an apparatus is added between the imaging plane of a main lens group of a camera and the imaging sensor of the camera. The apparatus includes a pupil matching lens located at the image plane of the main lens group of the camera. The apparatus further includes a kaleidoscope-like arrangement of mirrors which creates multiple views of the image passing through the pupil matching lens, each with a different perspective shift. The multiple images are then cast to the imaging sensor of the camera.

Figure 3:
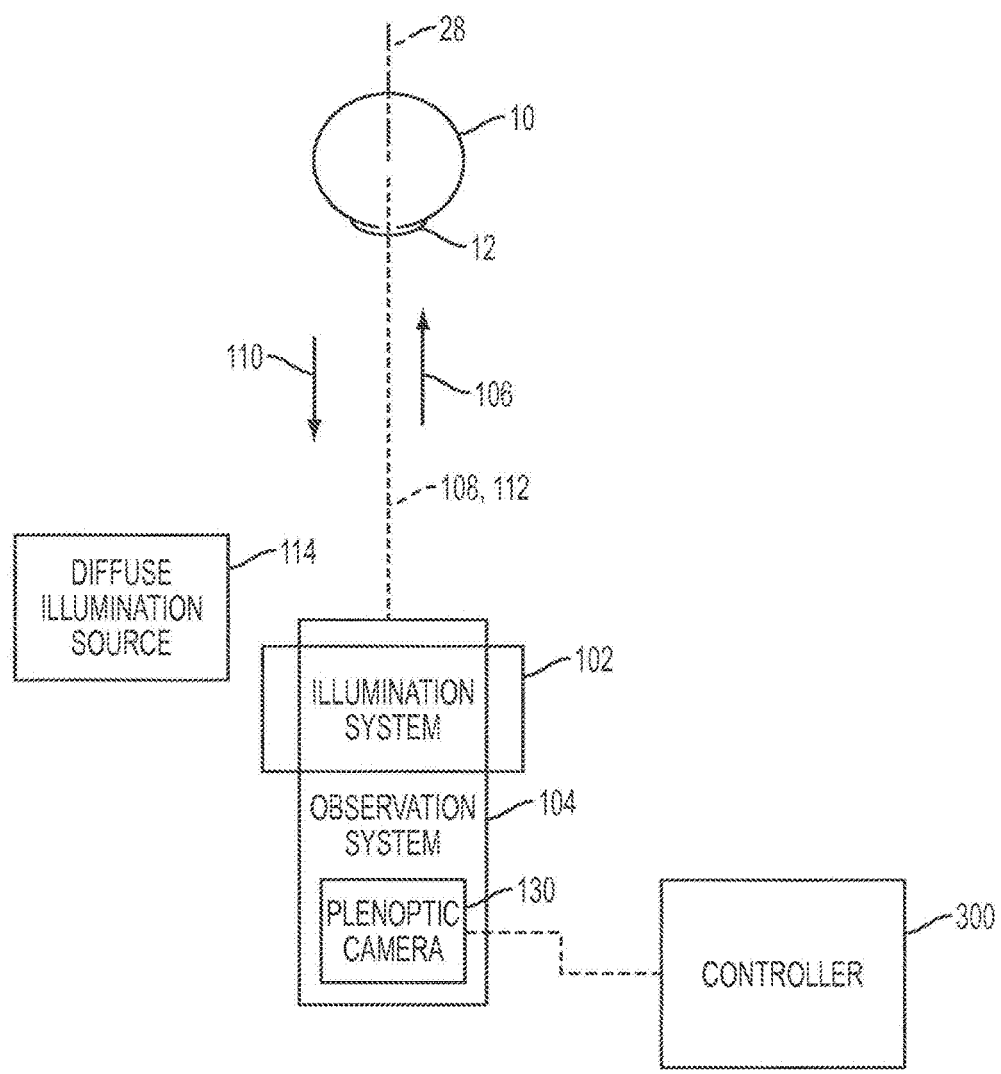
FIG. 3 illustrates the examination system of FIG. 2 with the optical axis of the illumination system being generally aligned with the optical axis of the observation system.

Referring to FIG. 3, examination system 100 is shown wherein optical axis 108 is generally coaxial with optical axis 112 and with optical axis 28 of the eye 10. Thus, observation system 104 is generally in line with illumination system 102. Although illumination system 102 and observation system 104 are shown being positioned directly in front of eye 10 and aligned with optical axis 28, illumination system 102 and observation system 104 may be angled relative to optical axis 28 of the eye 10, such as the position of illumination system 102 in FIG. 2. Further, the illumination system 102 and observation system 104 may be parallel with optical axis 28 of the eye, but offset from the optical axis 28 of the eye 10.

Figure 4:
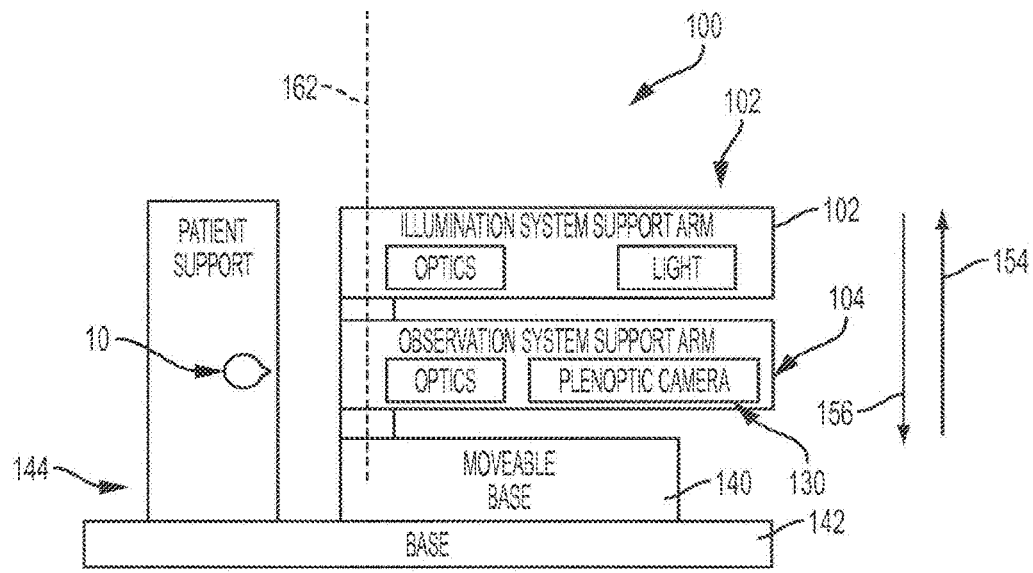
FIG. 4 illustrates a side view of an exemplary embodiment of the examination system of FIG. 2.
Figure 5:
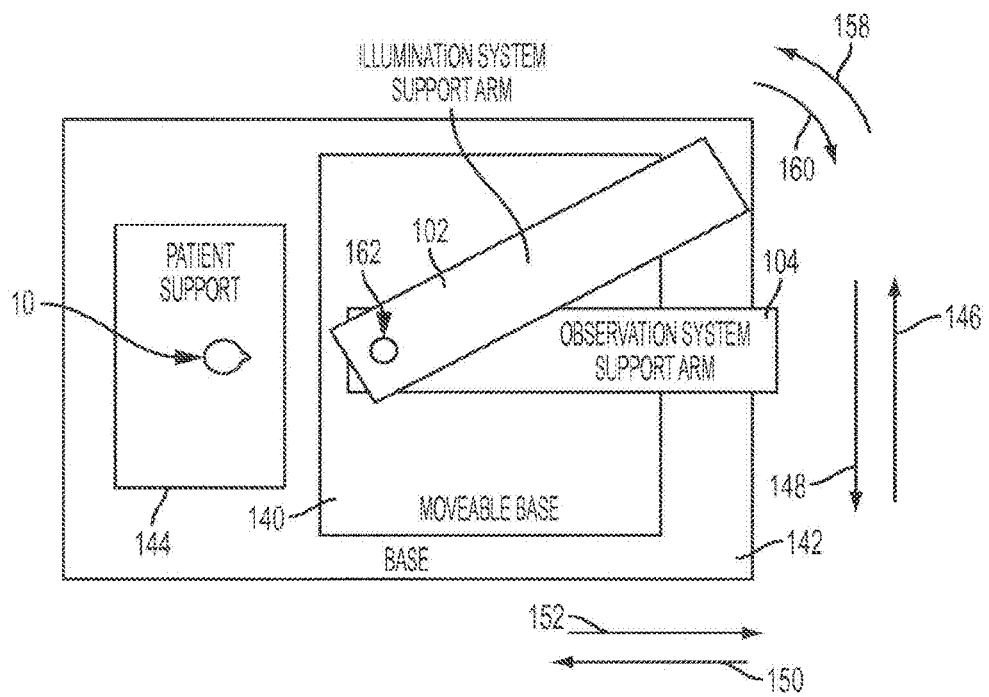
FIG. 5 illustrates a top view of the examination system of FIG. 4.

Referring to FIGS. 4 and 5, an exemplary embodiment of examination system 100 is shown. Illumination system 102 and observation system 104 are shown supported by a moveable base 140 which is supported on top of a base 142. In one embodiment, base 142 is the floor, a table-top, or an intermediate base which is supported by the floor or tabletop or other structure in an examination room. A patient support 144 is also supported by base 142. Patient support 144 positions an eye 10 of a patient relative to illumination system 102 and observation system 104.

Referring to FIG. 5, moveable base 140 is generally moveable in an x-axis in direction 146 and direction 148 relative to base 142 and in a z-axis in direction 150 and direction 152 relative to base 142. The movement of moveable base 140 relative to base 142 results in the movement of both illumination system 102 and observation system 104. In one embodiment, one of illumination system 102 and observation system 104 is not supported by moveable base 140 and thus does not move in concert with moveable base 140 when moveable base 140 is moved relative to base 142.

Illumination system 102 and observation system 104 are both moveable relative to moveable base 140 in a y-axis in direction 154 and direction 156 as illustrated in FIG. 4. Further, each of illumination system 102 and observation system 104 are rotatable relative to moveable base 140 in direction 158 and direction 160 as illustrated in FIG. 5. In the illustrated embodiment, each of illumination system 102 and observation system 104 are rotatable about an axis 162. Illumination system 102 and observation system 104 are individually rotatable relative to moveable base 140. As such, illumination system 102 may be rotated relative to moveable base 140 without a corresponding rotation of observation system 104 relative to moveable base 140 or vice versa.

Although illumination system 102 and observation system 104 are shown being rotatable about a vertical axis, axis 162, one or both of illumination system 102 and observation system 104 may be rotatable about a horizontal axis parallel to the x-axis or another axis in a plane defined by the x-axis and the y-axis. In one embodiment, each of illumination system 102 and observation system 104 is rotatable about a separate axis relative to moveable base 140.

Figure 6:
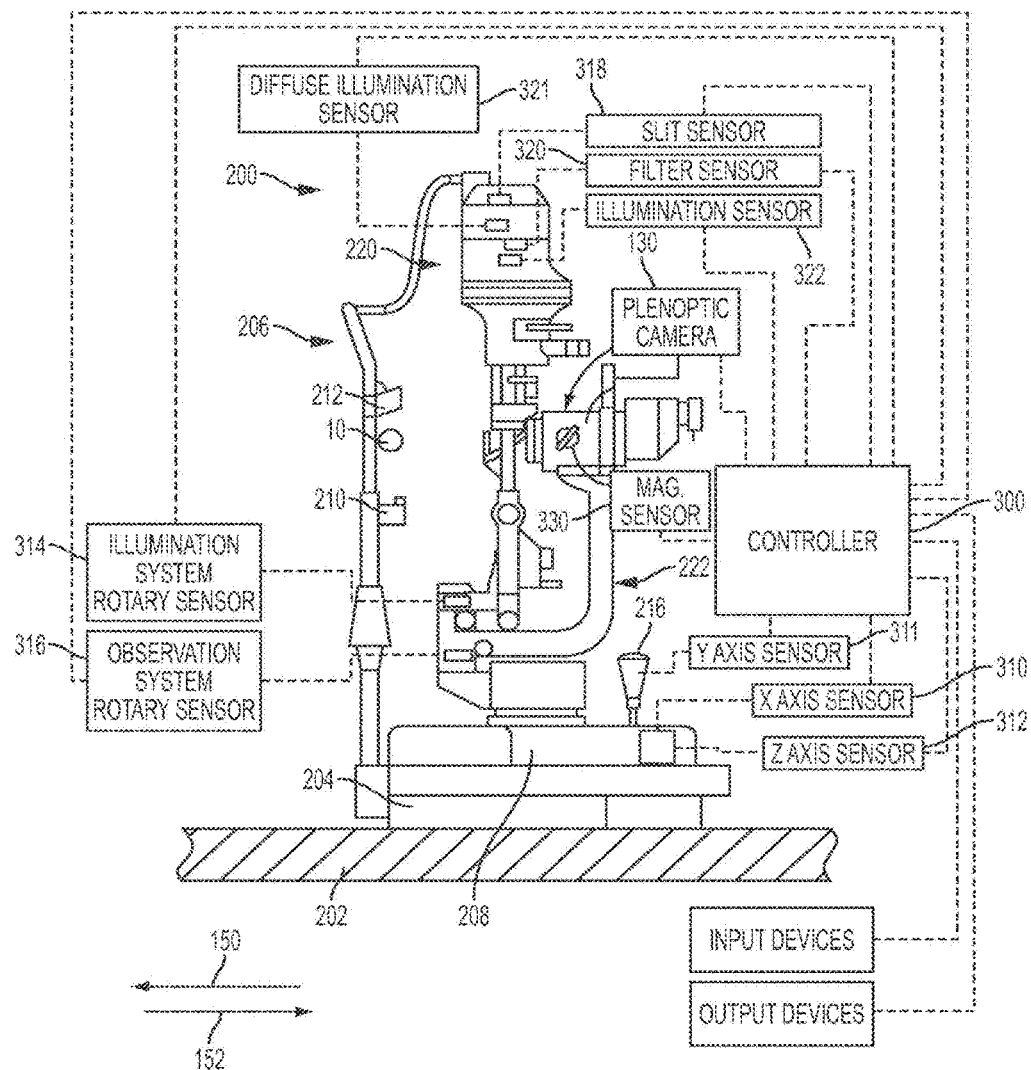
FIG. 6 illustrates an exemplary slit-lamp microscope of the present disclosure.

Referring to FIG. 6, an exemplary embodiment of examination system 100 is shown. A slit-lamp microscope 200 is illustrated in FIG. 6. Slit-lamp microscope 200 is supported on a base 202. Slit-lamp microscope 200 includes an intermediate base 204 supporting a patient support 206 and a moveable base 208. Patient support 206 includes a jaw support 210 and a forehead support 212 which support and position the eye 10 of the patient. Moveable base 208 is moveable relative to intermediate base 204 in the directions (x-axis and z-axis) discussed in connection with FIG. 5 for the movement of moveable base 140 relative to base 142. In one embodiment, moveable base 208 is moveable relative to intermediate base 204 in the x-axis, the y-axis, and the z-axis as discussed in connection with FIGS. 4 and 5. An exemplary system for movement in the y-axis is disclosed in U.S. Pat. No. 8,434,869, the disclosure of which is expressly incorporated by reference herein. In this embodiment, a movement in the y-direction is caused in response to a rotation of a knob 216 supported by the moveable base 208.

Moveable base 208 supports an illumination system 220 and an observation system 222. Illumination system 220 is moveable relative to moveable base 208 in the translation and rotation directions discussed in connection with FIGS. 4 and 5 for the movement of illumination system 102 relative to moveable base 140. Observation system 222 is moveable relative to moveable base 208 in the translation and rotation directions discussed in connection with FIGS. 4 and 5 for the movement of observation system 104 relative to moveable base 140. Illumination system 220 and observation system 222 are moveable relative to each other as discussed in connection with FIGS. 4 and 5 for the relative movement of illumination system 102 and observation system 104.

Figure 7:
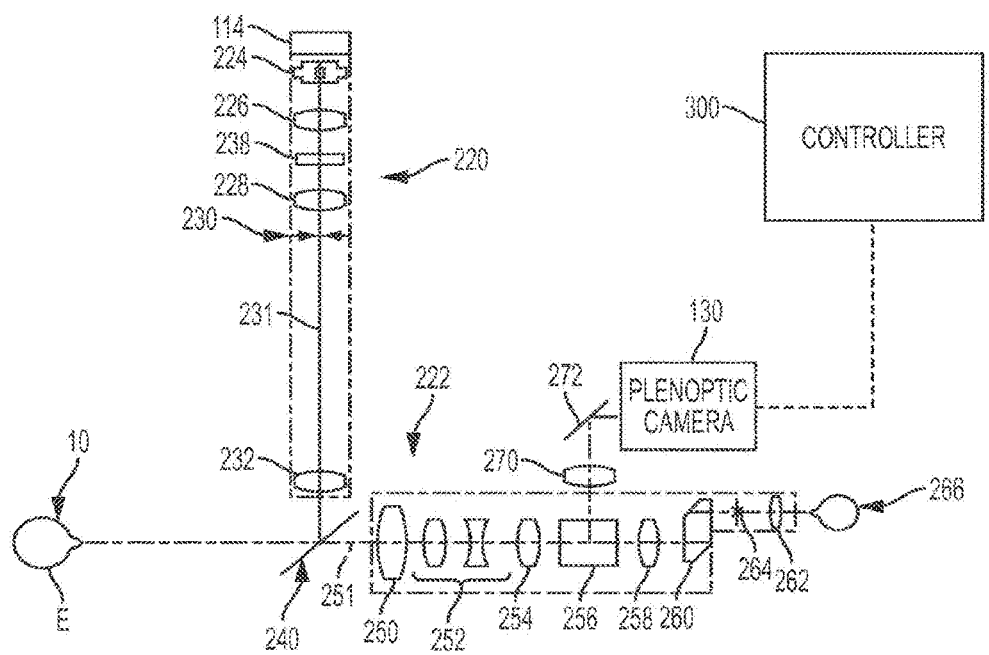
FIG. 7 illustrates an exemplary optical layout for the slit lamp microscope of FIG. 6.
Figure 8:
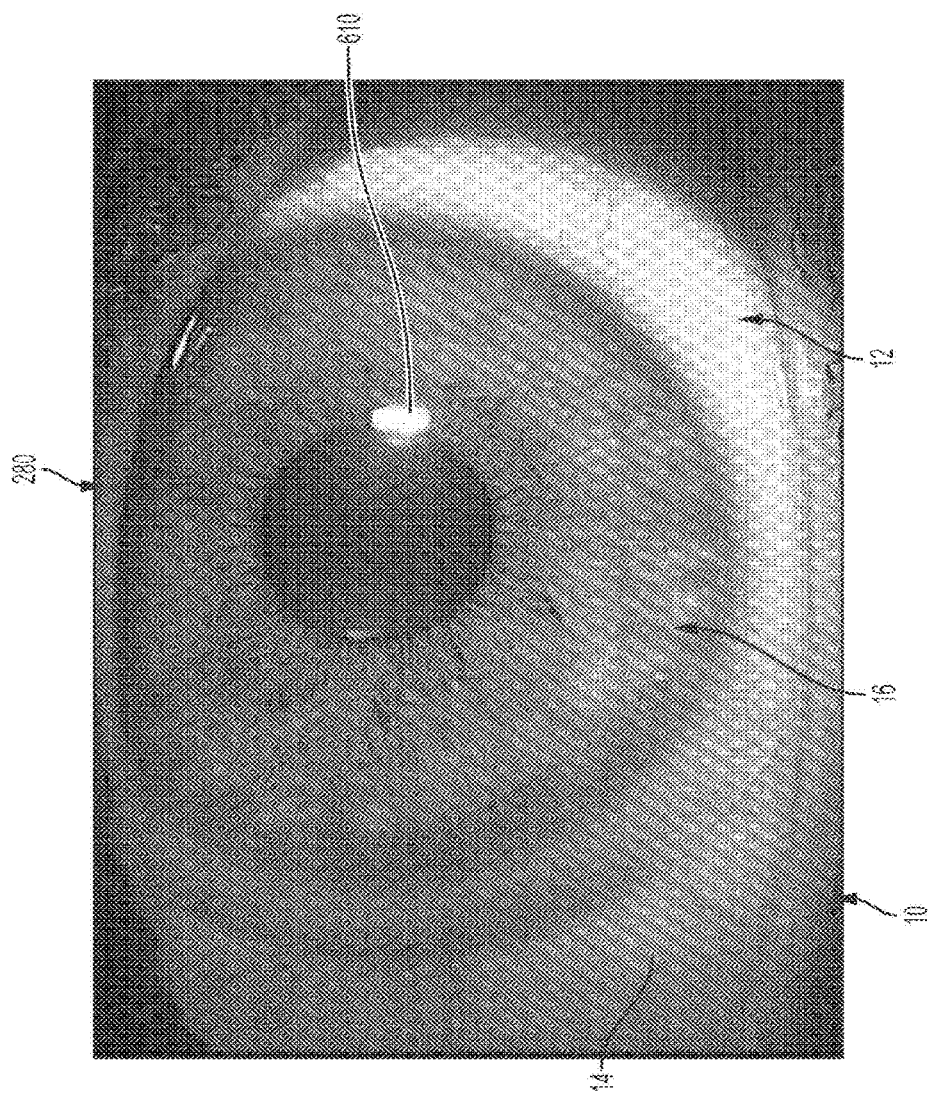
FIG. 8 illustrates an exemplary image of a fully illuminated (no slit) image of an eye under examination which may be obtained with the slit lamp microscope of FIG. 6.

Referring to FIG. 7, illumination system 220 includes a light source 224 and condenser lenses 226 and 228 for converging the light from the light source 224. Exemplary light sources include 224 a halogen lamp, an LED source, or other suitable light source. In one embodiment, illumination system 220 includes a strobe light source such as a xenon lamp. In one embodiment, illumination system 220 further includes a diffuse light illumination source 114. An example of the eye 10 illuminated with diffuse light illumination source 114 is shown in FIG. 8.

Illumination system 220 further includes a slit 230 for allowing only a part of the light passing through the condenser lenses 226 and 228 to pass through the slit 230 and out of illumination system 220. The light passing through slit 230 provides a narrow generally rectilinear beam of light 236 (see FIG. 9) which impinges upon eye 10 of the patient.

In one embodiment, illumination system 220 includes a filter 238 which limits the color of light that progresses through illumination system 220 and is ultimately used to illuminate eye 10. An exemplary filter would be cobalt blue to view fluorescein staining. Other exemplary filters may be used.

Slit 230 has an adjustable width to vary the width of the generally rectilinear beam of light which impinges upon eye 10 of the patient. In one embodiment, a width of slit 230 may be increased to provide generally full illumination of eye 10 of the patient. Exemplary widths for slit 230 are 1 mm and a thin slit having a width of up to about 1 mm. Further exemplary slit widths are in the range of about 0.2 mm to about 1.0 mm. In one embodiment, slit 230 is controlled through a knob or dial provided on illumination system 220. In one embodiment, slit 230 is automatically controlled through a computing system. An exemplary system for adjusting a width of slit 230 is provided in European Patent Application No. EP2695572, the disclosure of which is expressly incorporated by reference herein.

Illumination system 220 further includes a condenser lens 232 for converging the light that has passed through the slit 230 onto the eye 10 of the patient. The above-described slit 230 and the eye 10 to be examined are located in a conjugative position relative to the condenser lens 232 so that a local illumination ray of the slit 230 is projected to, for example, the cornea of the eye 10 to be examined. Light from slit 230 reaches eye 10 through a reflection from half-mirror 240. The light reflected from eye 10 is returned towards half-mirror 240 and passes through half-mirror 240 to reach observation system 222.

In one embodiment, illumination system 220 includes a collimator system which focuses the light from the source and then uses a collimator lens to produce a collimated beam of light emitting from light source 224. A portion of the collimated beam passes through slit 230 and is incident upon eye 10 of the patient. In one embodiment the light source is a white light source. In one embodiment the collimated beam is filtered to limit the color of the light that progresses through the illumination system and ultimately to illuminate eye 10.

Figure 26:
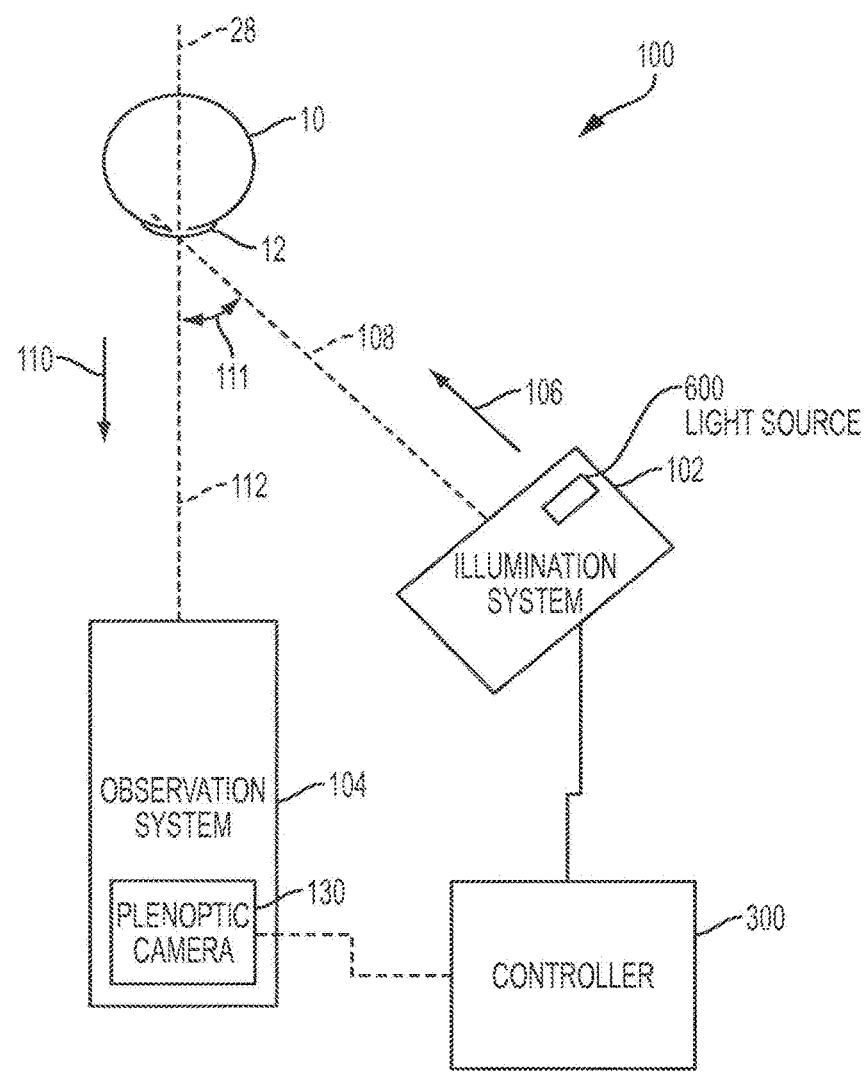
FIG. 26 illustrates an exemplary examination system of the present disclosure.
Figure 27:
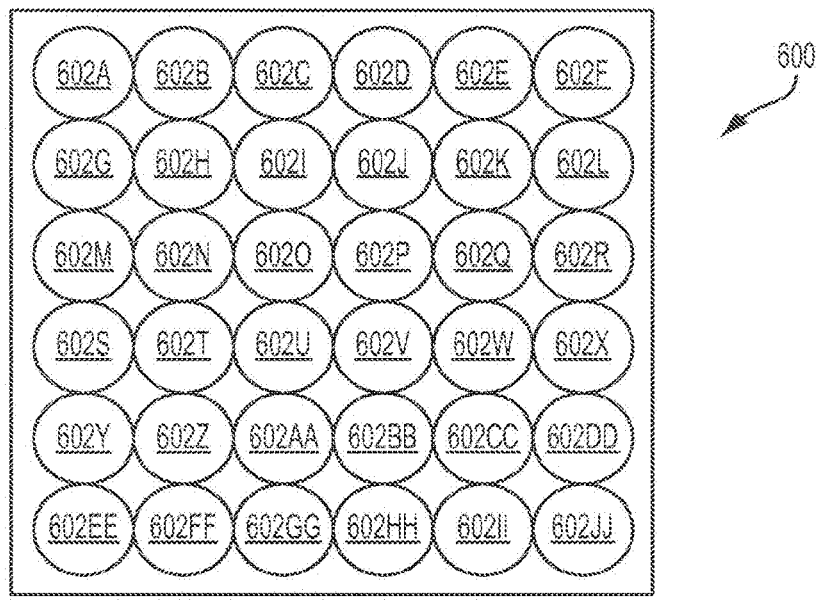
FIG. 27 illustrates an exemplary arrangement of a plurality of light sources of an illumination system.
Figure 28:
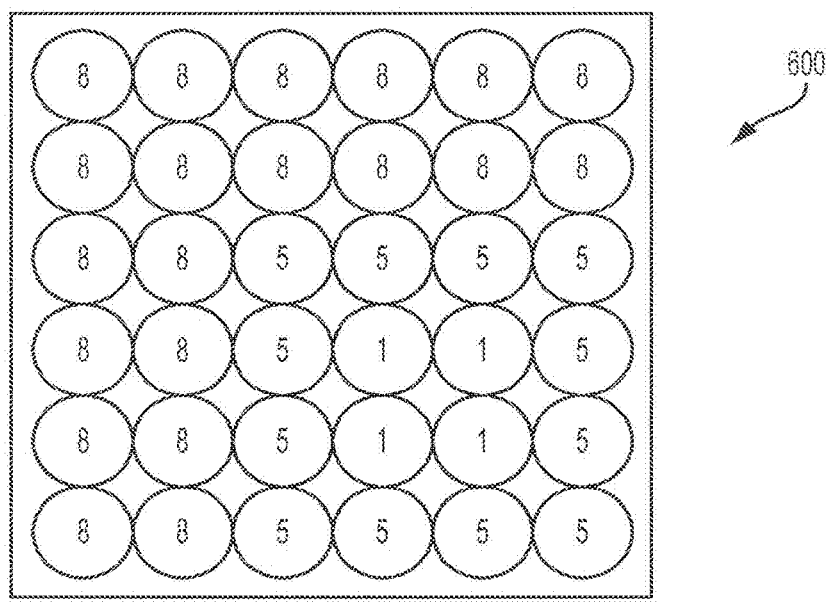
FIG. 28 illustrates an exemplary intensity level map for the plurality of light sources of FIG. 27.

In one embodiment, illumination system 220 includes light source 600 described in further detail herein with regard to FIGS. 26-28. As explained herein, light source 600 includes a plurality of individually controlled light sources whose optical characteristics may be adjusted to alter the illumination pattern on eye 10.

Observation system 222 includes an objective lens 250, a zooming optical system 252, a condenser lens 254, a beam splitter 256, a relay lens 258, a prism 260 for changing the optical path on the side of the housing of observation system 222 and an ocular lens 262. The image of the eye 10 is formed on an imaging point 264 and may be observed by the eye 266 of the person conducting the eye exam. The zooming optical system 252 changes a magnification of the image of eye 10.

Beamsplitter 256 also directs a portion of the light entering observation system 222 to a condenser lens 270 which directs the light into a plenoptic camera 130 through a reflection from a mirror 272. In one embodiment, plenoptic camera 130 is a still image camera. In one embodiment, plenoptic camera 130 is a video camera. In both embodiments, plenoptic camera 130 is used to capture a plurality of images of the eye 10 for subsequent examination as discussed herein. Plenoptic camera 130 captures both the position and direction of light propagating in space.

Referring to FIG. 8, an exemplary image 280 of eye 10 is shown. Image 280 is a fully illuminated (no slit) image of eye 10. In one embodiment, eye 10 is illuminated with diffuse light source 114. In one embodiment, eye 10 is illuminated with light source 224 and slit 230 is opened to a width to permit full illumination of the eye 10.

Figure 9:
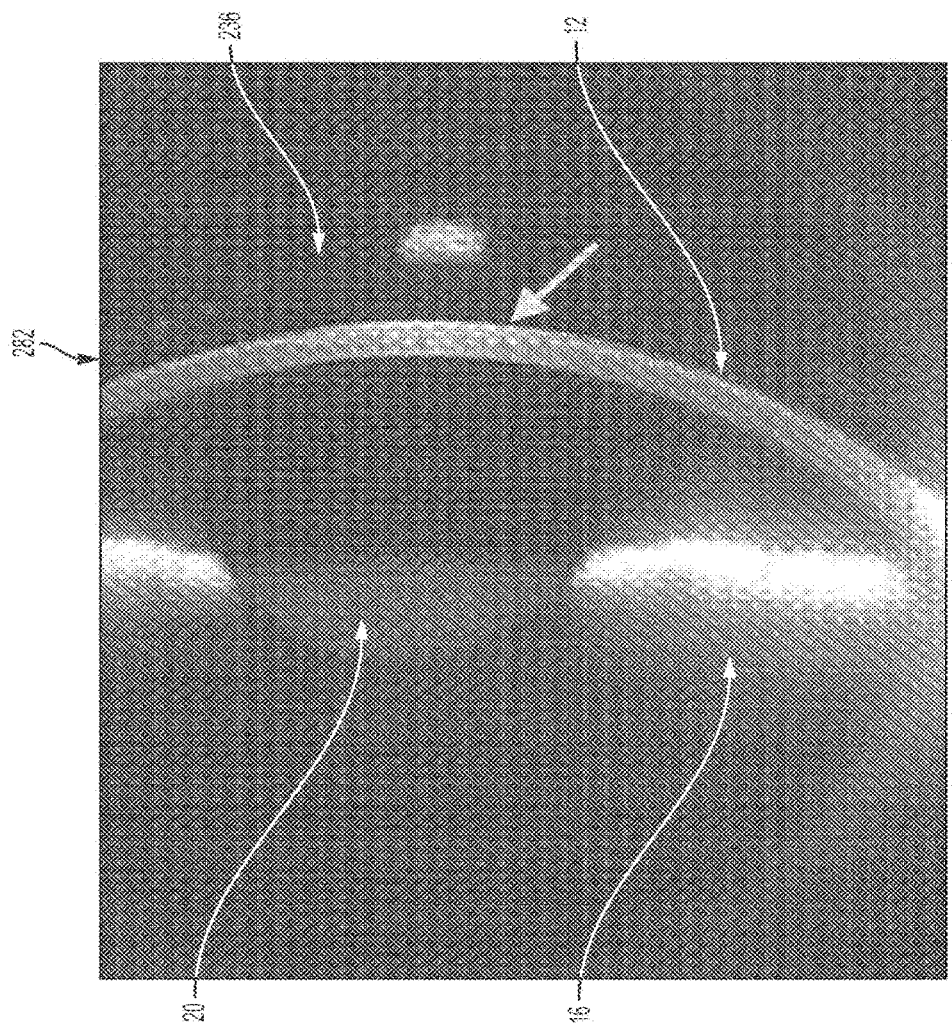
FIG. 9 illustrates an exemplary image of a slit of light focused on the cornea of an eye under examination which may be obtained with the slit lamp microscope of FIG. 6.

Referring to FIG. 9, an exemplary image 282 of eye 10 is shown. Image 282 illustrates a slit of light 236 focused on the cornea 12 of the eye 10. The focus depth of the slit of light 236 may be altered by moving moveable base 208 in either of direction 150 or direction 152. Further, the position of the slit of light 236 may be moved lateral relative to eye 10 by moving moveable base 208 in direction 146 or direction 148 and/or illumination system 220 in direction 158 or direction 160.

Figure 10:
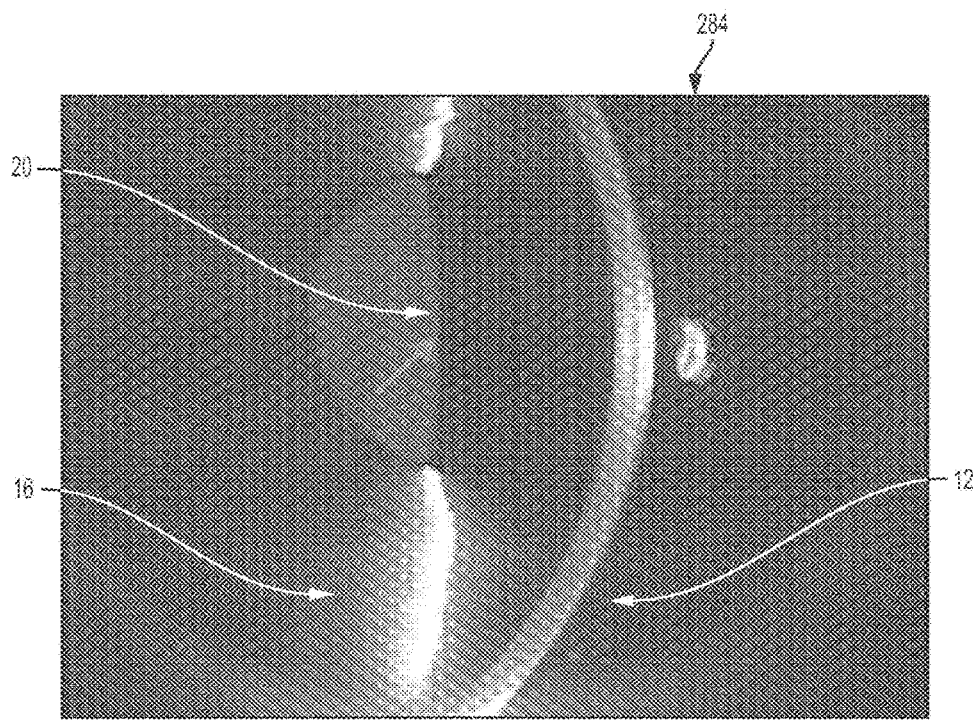
FIG. 10 illustrates an exemplary image of a slit of light focused on the front side of the lens of an eye under examination which may be obtained with the slit lamp microscope of FIG. 6.
Figure 11:
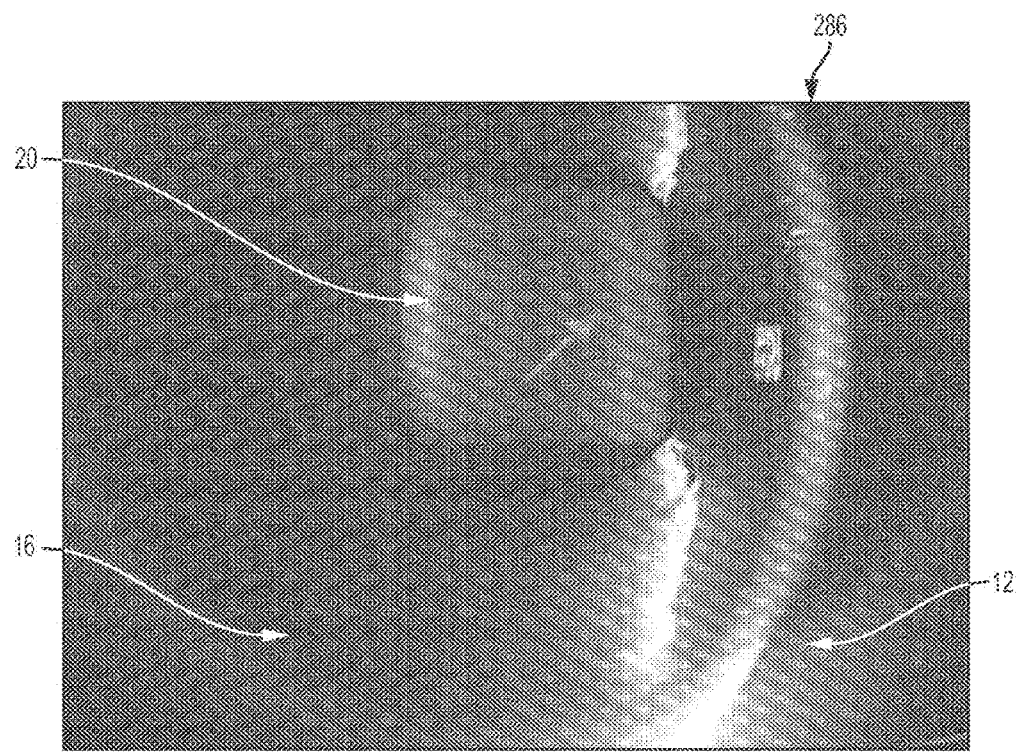
FIG. 11 illustrates an exemplary image of a slit of light illuminating a cross section of the lens of an eye under examination which may be obtained with the slit lamp microscope of FIG. 6.

Referring to FIG. 10, moveable base 208 is moved in direction 150 thereby focusing the slit of light 236 onto a front surface of the lens 18 of the eye. Referring to FIG. 11, moveable base 208 is moved further in direction 150 thereby illuminating a complete cross section of the lens 18 of the eye 10 with the slit of light 236.

Figure 12:
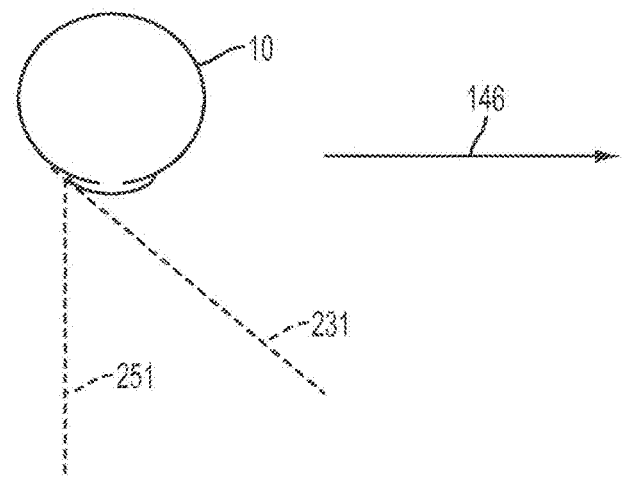
FIG. 12 illustrates an exemplary examination procedure with the slit lamp microscope of FIG. 6.
Figure 13:
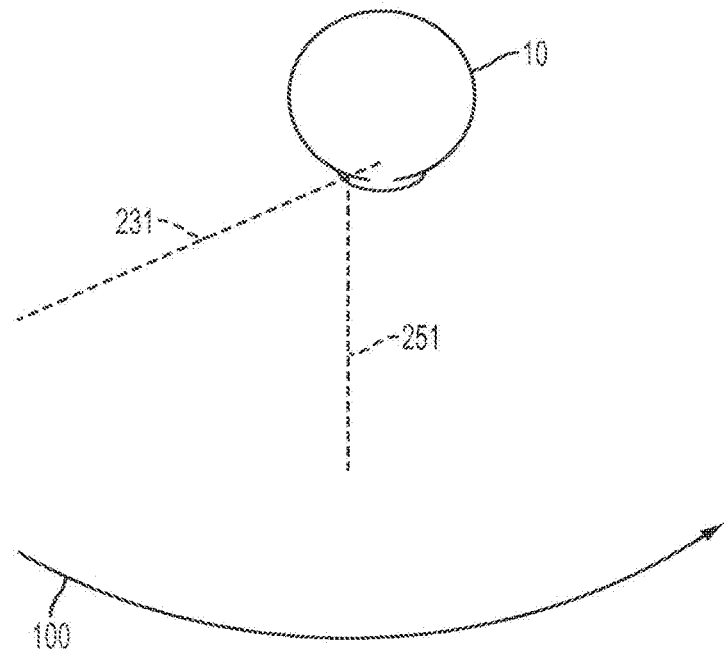
FIG. 13 illustrates another exemplary examination procedure with the slit lamp microscope of FIG. 6.

Ophthalmologists and optometrists typically examine the eye 10 by first horizontally scanning across the eye using various slit beam thicknesses and orientations to examine the most anterior structures such as the cornea and conjunctiva. FIG. 12 illustrates an exemplary scan across the eye 10 wherein the illumination system 220 and the observation system 222 are not rotated from an initial angular setting during the examination. FIG. 13 illustrates an exemplary scan of the eye 10 wherein the illumination system 220 is rotated relative to the observation system 222 during the examination.

Referring to FIG. 12, an exemplary examination which results in a movement of the slit of light 236 in direction 146 is shown. Slit-lamp microscope 200 is positioned such that an optical axis 231 (see FIG. 7) of illumination system 220 is angled relative to an optical axis 251 (see FIG. 7) of observation system 222. While maintaining illumination system 220 relative to observation system 222, moveable base 208 is moved in direction 146. In one embodiment, moveable base 208 is moved by an operator grasping a joystick input 216 (see FIG. 6). In one embodiment, moveable base 208 is moved automatically under the control of controller 300. In this embodiment, moveable base 208 includes one or more devices to move moveable base 208. Exemplary devices include motors, linear actuators, and other suitable devices. As moveable base 208 is moved in direction 146, the slit of light moves across eye 10. An example with the slit of light illustratively marked as line of light 450 is represented in the images shown in FIGS. 16-23 which are discussed in further detail herein.

Referring to FIG. 13, an exemplary movement of the slit of light 236 in direction 158 is shown. Slit-lamp microscope 200 is positioned such that an optical axis 231 of illumination system 220 is angled relative to an optical axis 251 of observation system 222. While maintaining observation system 222 relative to moveable base 208, illumination system 220 is moved in direction 158. In one embodiment, illumination system 220 is moved by an operator grasping the support structure of illumination system 220 and rotating illumination system 220 about axis 162. In one embodiment, illumination system 220 is moved automatically under the control of controller 300. In this embodiment, illumination system 220 includes one or more devices to move the illumination system 220 relative to the moveable base 208. Exemplary devices include motors and other suitable devices. As illumination system 220 is moved in direction 158, the slit of light 236 moves across eye 10.

Returning to FIG. 6, in the illustrated embodiment, controller 300 monitors the use of slit-lamp microscope 200. Slit-lamp microscope 200 includes a plurality of sensors that provide an indication of a setting, a position, or other characteristic of one or more components of slit-lamp microscope 200. For example, moveable base 208 may support an x-axis sensor 310 and a z-axis sensor 312 which provide an indication of the position of moveable base 208 relative to intermediate base 204. Exemplary sensors include optical sensors, mechanical sensors, electrical sensors, and combinations thereof. In one example, a computer mouse style trackball is received in a pocket in the bottom of moveable base 208. The trackball rolls as moveable base 208 is moved in any one of direction 146, direction 148, direction 150, and direction 152. Sensors 310 and 312 monitor the movement of the trackball and provide an indication of the position of moveable base 208 to controller 300. A y-axis sensor 311 provides an indication of the position of illumination system 220 and observation system 222 relative to moveable base 208. In one embodiment, sensor 311 monitors a rotation of joystick input 216 which elevates or lowers the illumination system 220 and observation system 222. The internal mechanism of joystick input 216 may be an inclined spiral thread.

Further, moveable base 208 may support an illumination system rotary sensor 314 and an observation system rotary sensor 316. Illumination system rotary sensor 314 monitors a rotation of illumination system 220 relative to moveable base 208. Observation system rotary sensor 316 monitors a rotation of observation system 222 relative to moveable base 208. Exemplary sensors include optical sensors, mechanical sensors, electrical sensors, and combinations thereof.

Slit-lamp microscope 200 further includes a slit sensor 318, a filter sensor 320, a diffuse light illumination sensor 321, and an illumination sensor 322. Slit sensor 318 provides an indication of a slit width setting of slit 230. An exemplary system for monitoring a slit width is disclosed in European Patent Application No. EP2695572, the disclosure of which is expressly incorporated by reference herein. Filter sensor 320 provides an indication of whether a filter is placed in the light beam of illumination system 220. In one embodiment, a filter wheel is provided and an angular position of the filter wheel is monitored. Diffuse light illumination sensor provides an indication of the background illumination power level of a diffuse light source 114 (see FIG. 7). Illumination sensor 322 provides an indication of a power intensity of light source 224. Slit-lamp microscope 200 further includes a magnification sensor 330 which provides an indication of a magnification setting of zooming optical system 252 of observation system 222.

In one embodiment, one or more of moveable base 208, illumination system 220, observation system 222, slit 230, filter 238, light source 224, zooming optical system 252, and other settings of slit-lamp microscope 200 are set through manual inputs. In one embodiment, one or more of moveable base 208, illumination system 220, observation system 222, slit 230, filter 238, light source 224, zooming optical system 252, and other settings of slit-lamp microscope 200 are set by controller 300 controlling motors or other actuators.

Figure 14:
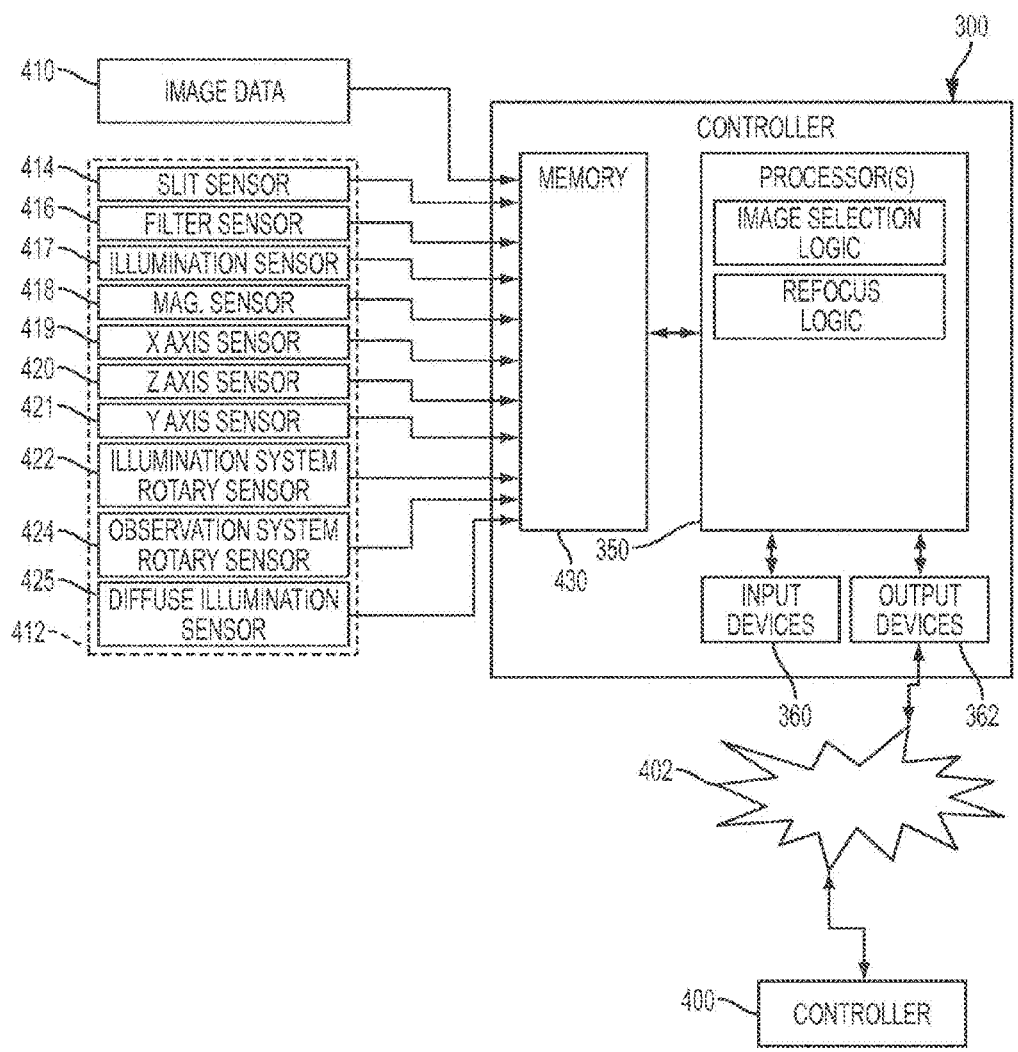
FIG. 14 illustrates an exemplary controller of the slit lamp microscope of FIG. 6 and an exemplary remote controller.

Referring to FIG. 14, controller 300 includes one or more processors 350 configured to execute instructions stored in memory 430 for receiving images from plenoptic camera 130 and sensor information from moveable base 208, illumination system 220, observation system 222, slit 230, filter 238, light source 224, zooming optical system 252. In addition, patient information 354 and examination information 356 may be stored in memory 430.

Controller 300 includes one or more input devices 360 to receive input from an operator of slit-lamp microscope 200. Exemplary input devices include keys, buttons, joysticks, touch screens, dials, switches, mouse, and trackballs which providing user control of slit-lamp microscope 200. Controller 300 further includes one or more output devices 362 to provide feedback or information to an operator. Exemplary output devices include a display, lights, and/or audio devices which provide user feedback or information.

In one embodiment, the information stored in memory 430 is made available to additional controllers, illustratively controller 400, over a network 402. In one embodiment, the logic of controller 300 is also made available to controller 400 over network 402. An exemplary output device 362 of controller 300 is a network access device which is capable of accessing network 402. An exemplary network access device is a modem.

Controller 400 includes input devices and output devices to receive input from an operator and to provide feedback or information to the operator, respectively. An exemplary operator for controller 400 is an ophthalmologist located remote from slit-lamp microscope 200. In one embodiment, controller 400 includes the logic described herein of controller 300 and retrieves images and related information over network 402 from controller 300. This arrangement allows an ophthalmologist to review examination data remotely from the slit-lamp microscope 200. In this manner an ophthalmologist is able to review a slit lamp exam remote from slit-lamp microscope 200. Further, since the images obtained during the initial examination or derived from the initial examination are stored on a memory of controller 400 or a memory accessible by controller 400 the ophthalmologist make review the slit lamp examination at a later time than the original examination.

As shown in FIG. 14, controller 300 receives a plurality of images 410 from plenoptic camera 130. For each image 410, controller 300 also receives sensor data 412 related to one or more characteristics of slit-lamp microscope 200. Exemplary sensor data includes slit sensor data 414 from slit sensor 318, filter sensor data 416 from filter sensor 320, illumination sensor data 417 from illumination sensor 322, magnification sensor data 418 from magnification sensor 330, x-axis sensor data 419 from x-axis sensor 310, y-axis sensor data 421 from y-axis sensor 311, z-axis sensor data 420 from z-axis sensor 312, illumination system rotary sensor information 422 from illumination system rotary sensor 314, observation system rotary sensor information 424 from observation system rotary sensor 316, and diffuse illumination sensor 425 from diffuse illumination sensor 321.

The plurality of images 410 and sensor data 412 is stored in memory 430. Memory 430 may include, but is not limited to, memory associated with the execution of software and memory associated with the storage of data. Memory 430 includes non-transitory computer readable media. Computer-readable media may be any available media that may be accessed by one or more processors of controller 300 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by controller 300.

In one embodiment, memory 430 also stores patient information 432 and examination information 434. Exemplary patient information includes a patient name or other identifier, patient medical history, and other suitable information. Exemplary examination information includes eye being examined, additional settings of slit-lamp microscope 200, and other suitable information. In one embodiment, controller 400 also includes or has access to image data 410 and sensor data 412 along with the logic of controller 300. As such, the discussions herein related to controller 300 apply equally to a remotely located controller, such as controller 400.

Figure 15:
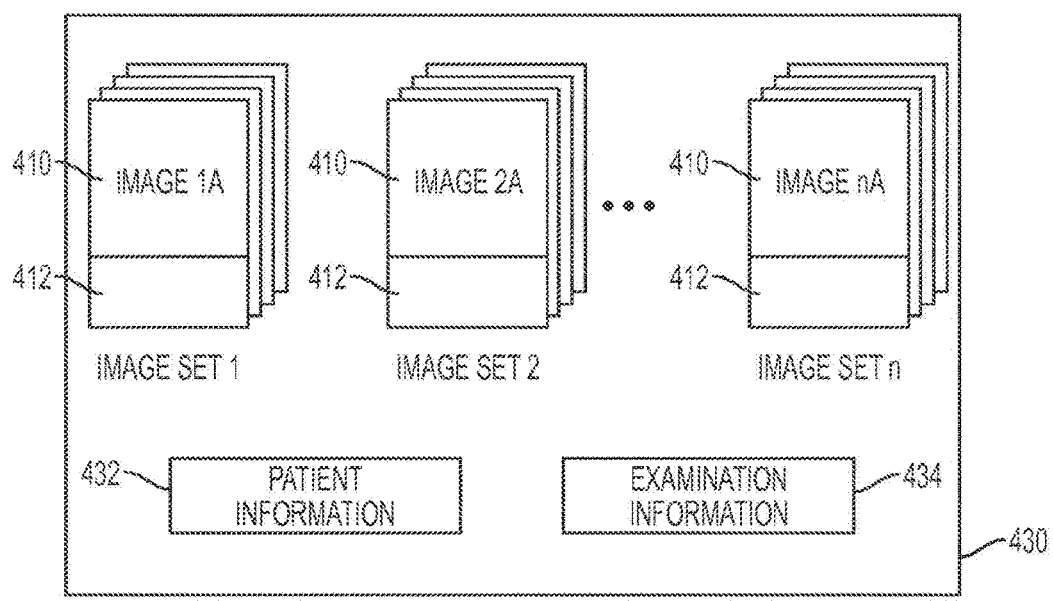
FIG. 15 illustrates an exemplary arrangement of information stored for an examination with the slit lamp microscope of FIG. 6.

Referring to FIG. 15, a plurality of images may be grouped together. In FIG. 15, three groups of images, Image Set 1, Image Set 2, and Image Set n are illustrated. Sensor information 412 is provided for each of the images. In one embodiment, plenoptic camera 130 records a video and the video clip is the image set which includes a plurality of frames. In one embodiment, plenoptic camera 130 records still images and the operator of slit-lamp microscope 200 signals with one of input devices 360 when to capture a still image. In one embodiment, plenoptic camera 130 records still images and controller 300 automatically captures images corresponding to various preset sensor readings. For example, when illumination system 220 is being rotated in direction 158, controller 300 may execute logic to capture an image at set angular values of illumination system rotary sensor 314.

Figure 16:
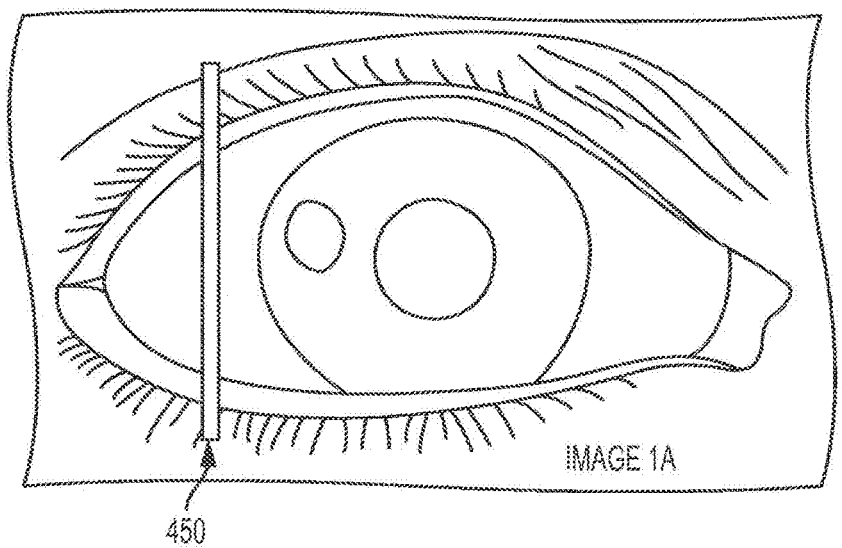
FIG. 16 illustrates an exemplary image of a slit of light illuminating a portion of the conjunctiva on a first side of the pupil which may be obtained with the slit lamp microscope of FIG. 6 while performing the examination procedure of FIG. 12.
Figure 17:
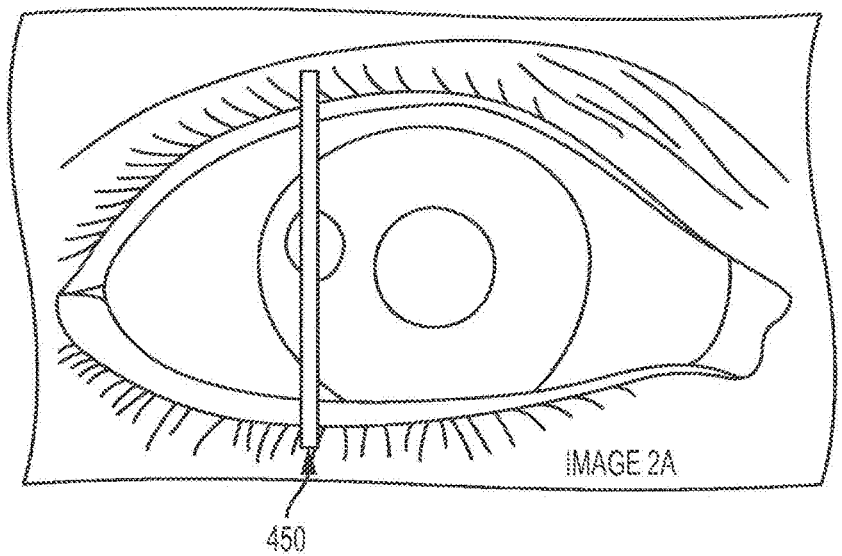
FIG. 17 illustrates an exemplary image of a slit of light illuminating a portion of the iris on the first side of the pupil which may be obtained with the slit lamp microscope of FIG. 6 while performing the examination procedure of FIG. 12.
Figure 18:
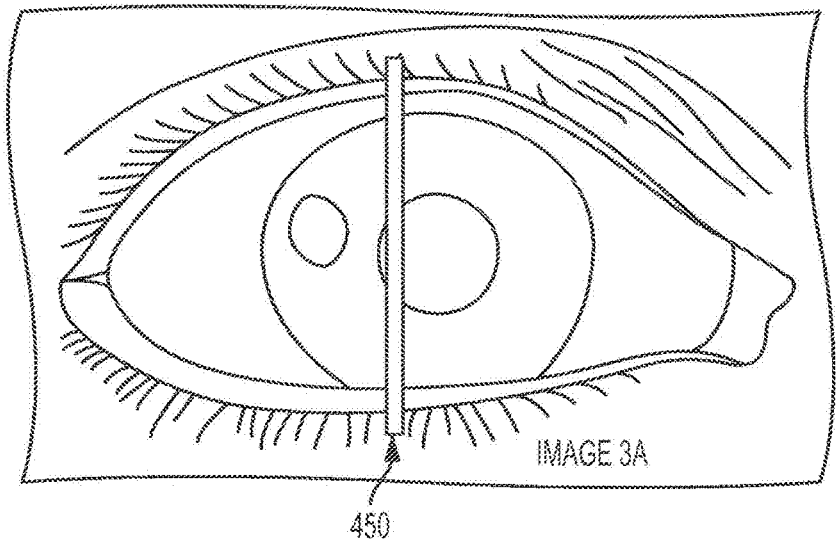
FIG. 18 illustrates an exemplary image of a slit of light illuminating a portion of the iris on at a first side edge of the pupil which may be obtained with the slit lamp microscope of FIG. 6 while performing the examination procedure of FIG. 12.
Figure 19:
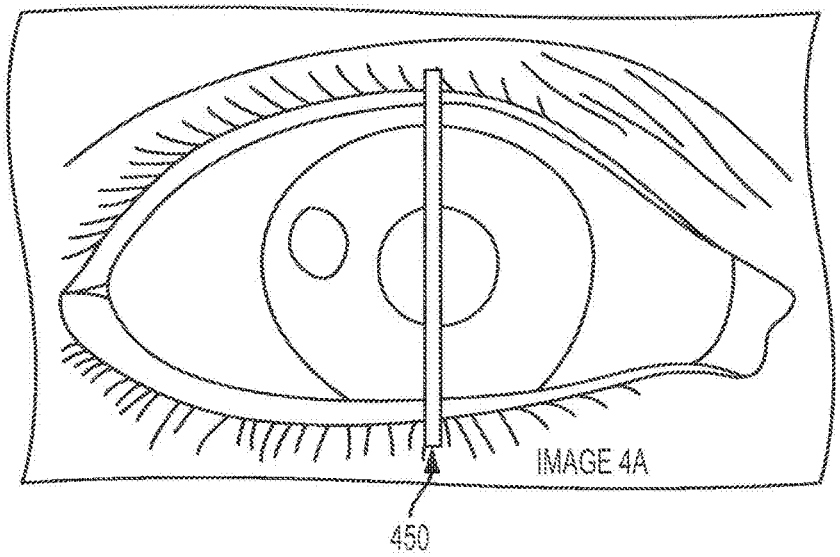
FIG. 19 illustrates an exemplary image of a slit of light illuminating a portion of the iris at the center of the pupil which may be obtained with the slit lamp microscope of FIG. 6 while performing the examination procedure of FIG. 12.
Figure 20:
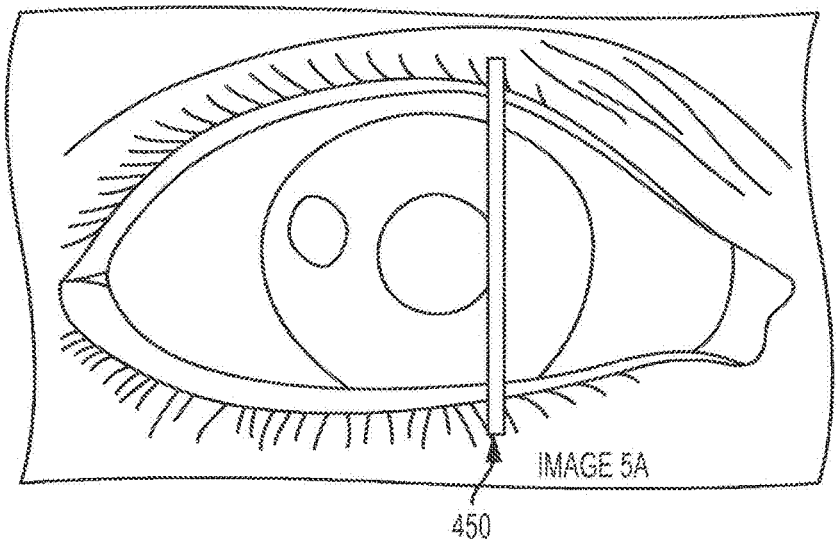
FIG. 20 illustrates an exemplary image of a slit of light illuminating a portion of the iris on at a second side edge of the pupil which may be obtained with the slit lamp microscope of FIG. 6 while performing the examination procedure of FIG. 12.
Figure 21:
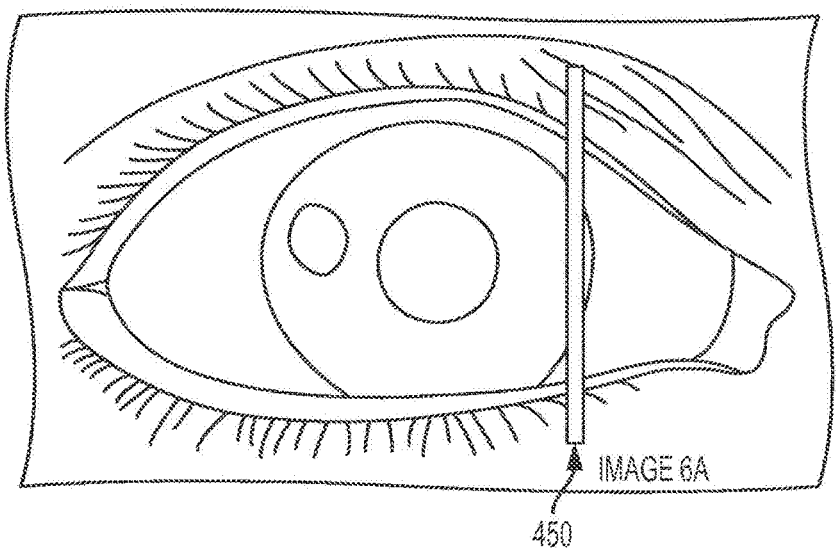
FIG. 21 illustrates an exemplary image of a slit of light illuminating a portion of the iris on the second side of the pupil which may be obtained with the slit lamp microscope of FIG. 6 while performing the examination procedure of FIG. 12.

An exemplary representation of Image Set 1 is provided in FIGS. 16-23. Referring to FIG. 16, Image 1A of Image Set 1 is shown. In Image 1A a line of light 450 produced by slit 230 is shown being positioned to the left of iris 16. Advancing through Images 2A through 6A, line of light 450 moves to the right, as shown in FIGS. 17-23. This movement of line of light 450 to the right is due to a movement of moveable base 208 in direction 146.

The slit lamp microscope apparatus 200 described in this application permits a technician with basic skills to obtain the light-field data needed to recreate a slit-lamp examination at a later time and in a different location. The light-field camera captures an image at a given slit-beam size and angular orientation. A motorized apparatus moves the slit-beam along a horizontal axis to an adjacent or an overlapping position where another high resolution light-field image would be obtained. This process is repeated multiple times to scan across the structures of the eye. This scanning process can be repeated with slit-beams of various widths and angles of incidence to simulate the types of views obtained by an ophthalmologist using a traditional slit-lamp. This scanning allows for libraries of adjacent light-field slit images to be created for the various slit-beam widths and angles.

Retroillumination and specular reflection views are also possible through the careful placement of the illumination source and the viewing angle of the plenoptic camera 130. Non-slit illumination such as a ring light or point-source of light can be utilized in a similar manner (especially for retroillumination through a pupil). During light-field data acquisition, images are evaluated in real time to discard errant images, for example those associated with patient blinking, glare or patient movement. One embodiment of the apparatus includes soft arms that contact the upper and/or lower lids to allow for blink-free imaging. Stabilization algorithms that use landmarks of the eye and other stabilization techniques may be used to improve both image quality and the ability to collate adjacent images for later display. In one embodiment, images are captured with illumination system 220 positioned at −45° from straight on center (see FIG. 13), straight on center, and 45° from straight on center. For each setting of the illumination system 220 the slit is moved across all the features in the eye as well as maybe changing the angle (maybe not) for each one field illumination.

In one embodiment of the apparatus, the images obtained by the light-field camera are analyzed in real-time to automatically place the focus of the slit beam at various clinically important anatomic structures of the eye. These can include the tear film, anterior cornea, posterior cornea, the anterior chamber midpoint, anterior lens capsule, central lens, posterior lens capsule. Although these focal planes can be retrospectively viewed with light-field processing, thin slit-beam illumination may not be simultaneously focused at each of these layers (unless collimated light is used).

Other embodiments of the apparatus allow for variable angles of examination. The typical slit-lamp sequence is performed with vertically oriented slit-beams and horizontal movement of the viewing oculars, but the orientation of the examination could be rotated 90 degrees (horizontal slit/vertical scanning) or to any oblique angle. Various combinations of slit-beam focal plane, slit size and angular orientation imaging can be pre-chosen via the apparatus software to balance the ophthalmic completeness of the examination and the computational demands required to recreate various slit-beam views.

Figure 22:
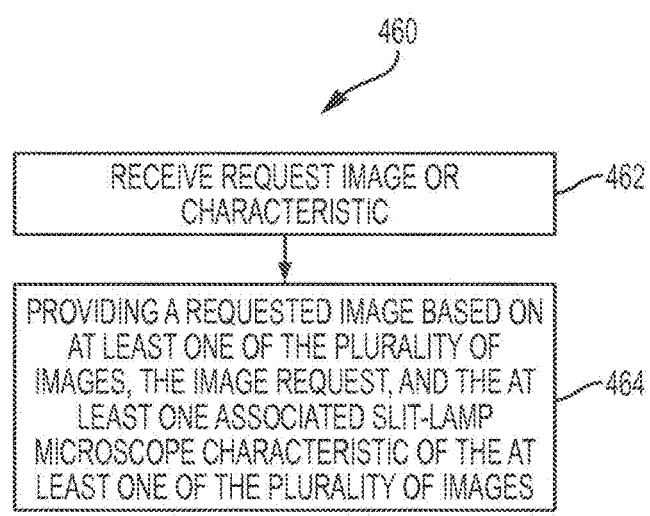
FIG. 22 illustrates an exemplary processing sequence of a controller of the present disclosure.

Referring to FIG. 22, an exemplary processing sequence 460 of controller 300 is illustrated. Controller 300 receives a request for an image or a characteristic, as represented by block 462. Controller 300 provides a requested image based on at least one of the plurality of images, the image request, and the associated slit-lamp microscope characteristic of the at least one of the plurality of images, as represented by block 464.

In one example, a user through input devices 360 (or the respective input devices of controller 400) requests a specific image or image set to be displayed. For instance, a user may want to first walk through the examination as it was taken. Thus, the user may request the first image of Image Set 1. In this case image selection logic 460 would return the first image of Image Set 1.

In another example, the user through input devices 360 (or the respective input devices of controller 400) requests the image closest to a given characteristic of slit-lamp microscope 200. For instance, the user may want an image at the same x,y,z positioning of slit-lamp microscope 200, but with a narrower slit width. In this case image selection logic 460 would search the sensor data 412 stored in memory 430 to determine which image has the closest x,y,z, position and a narrower slit width.

Figure 23:
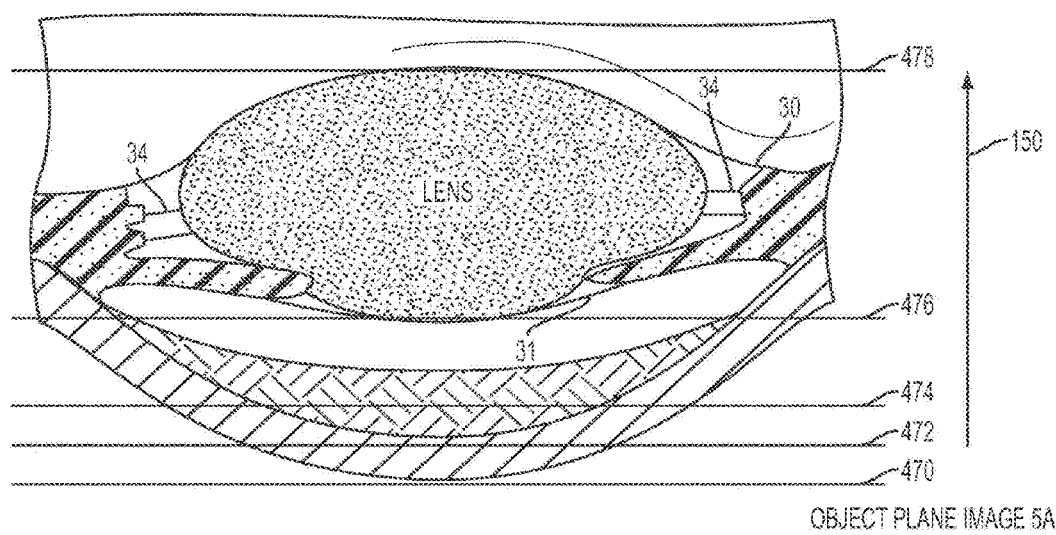
FIG. 23 illustrates an example of refocusing with the system of the present disclosure.

In a further example, the user requests an image offset from the current image in one of x,y,z or the rotational angle of illumination system 220 or observation system 222. For instance, the user may want an image at the same x,y positioning of slit-lamp microscope 200, but focused deeper into the eye along the z-axis. Referring to FIG. 23, the object plane of Image 5A is represented by line 470. Image 5A is generally focused along the z-axis on the cornea 12 of the eye 10. The user may want to step through the eye 10 in direction 150 (deeper in the z-axis) as represented by lines 472-478. In this case refocus logic 480 of controller 300 would utilize the "light field" data of the image to refocus at the requested z-depth. The systems and methods related to a variety of image reconstruction techniques using light-field data are provided in US Patent Publication 2009/0041448 (Georgiev), U.S. Pat. No. 7,936,392 (Ng), and the remaining patents and published applications identified herein, the entire disclosures of which are incorporated by reference herein. In another instance, the user may want an image at the same y,z positioning of slit-lamp microscope 200, but offset in the x-direction. Assuming another image is not already offset in the x-axis by the requested amount, perspective change logic 480 changes the perspective of the eye 10 along the x-axis. The systems and methods related to a variety of image reconstruction techniques using light-field data are provided in US Patent Publication 2009/0041448 (Georgiev), U.S. Pat. No. 7,936,392 (Ng), and the remaining patents and published applications identified herein, the entire disclosures of which are incorporated by reference herein. In one embodiment, controller 300 may provide Scheimplug images of the eye from the light field data to provide different perspective views of the various structures of the eyes.

In a still further example, the user may request that multiple images be combined into a focal stack image wherein the in-focus portions of multiple image are combined or otherwise displayed together to generate an image having multiple depths along the z-axis in focus. In one example, the user may want to combine portions of multiple images, either taken during the examination or generated from the light field data, together to generate a focused image of a curved structure of the eye 10 which extends along the z-axis, such as the cornea 12 of the eye 10.

Figure 24A:
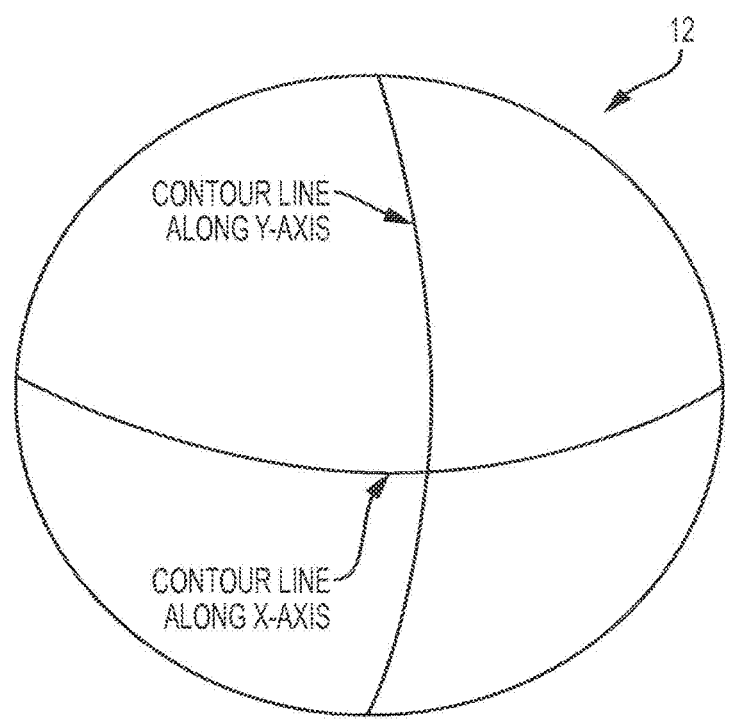
Figure 24D:
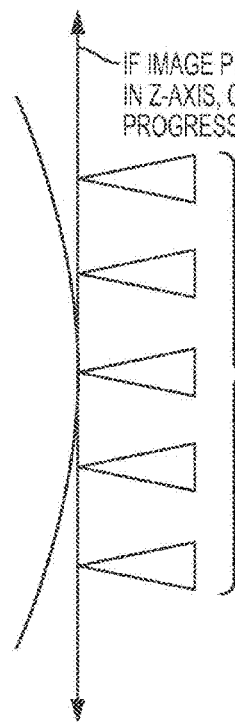
Figure 24E:
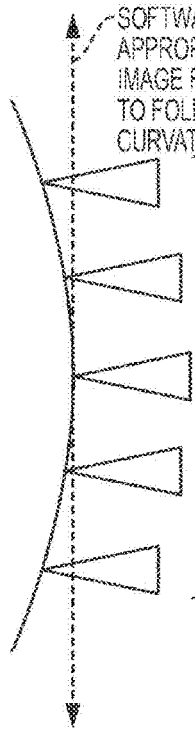

In yet still a further example, the user may want to selectively focus the z-axis on a clinically important structure such as the anterior cornea 12, so that x or y axis movements would follow the curved anatomy of the cornea. Referring to FIG. 24A, a representation of the anterior cornea 12 is shown. Referring to FIG. 24B, an example is shown for the slit positions corresponding to FIGS. 19-21 wherein the software logic does not use the light field data to refocus in the z-direction as slit 450 is moved along the x-direction. In contrast, as shown in FIG. 24C, an example is shown for the slit 450 positions corresponding to FIGS. 19-21 wherein the software logic does use the light field data to refocus in the z-direction as slit 450 is moved along the x-direction. Thus, instead of simply simulating a horizontal movement of the slit lamp, controller 300 or 400 would focus posteriorly slightly as the exam moved away from the corneal apex towards the peripheral cornea in order to follow the corneal curvature. In another embodiment of the apparatus, the software logic would use light-field data to selectively focus the image along the curved y-direction of the cornea in the same manner as illustrated for the x-direction, so that instead of focusing in one plane, the focus could be "wrapped" along the curved surface of the eye. Referring to FIG. 24D, an example is shown of the focus plane in the Y direction for the slit position shown in FIG. 20 (the line of light is represented at five discrete points for purposes of illustration) wherein the software logic does not use the light field data to refocus in the z-direction. In contrast, as shown in FIG. 24E, an example is shown for the slit position shown in FIG. 20 wherein the software logic does use the light field data to refocus in the z-direction. Thus, controller 300 or 400 would focus posteriorly slightly for positions offset from the corneal apex in the y-direction in order to follow the corneal curvature. In one embodiment, the software logic uses the light field data to bring the entire cornea into focus by following the corneal curvature in both the x-direction and the y-direction. In one embodiment, controller 300 or 400 assumes the corneal curvature to have a 7.8 mm radius of curvature in the defocus calculations.

Figure 25:
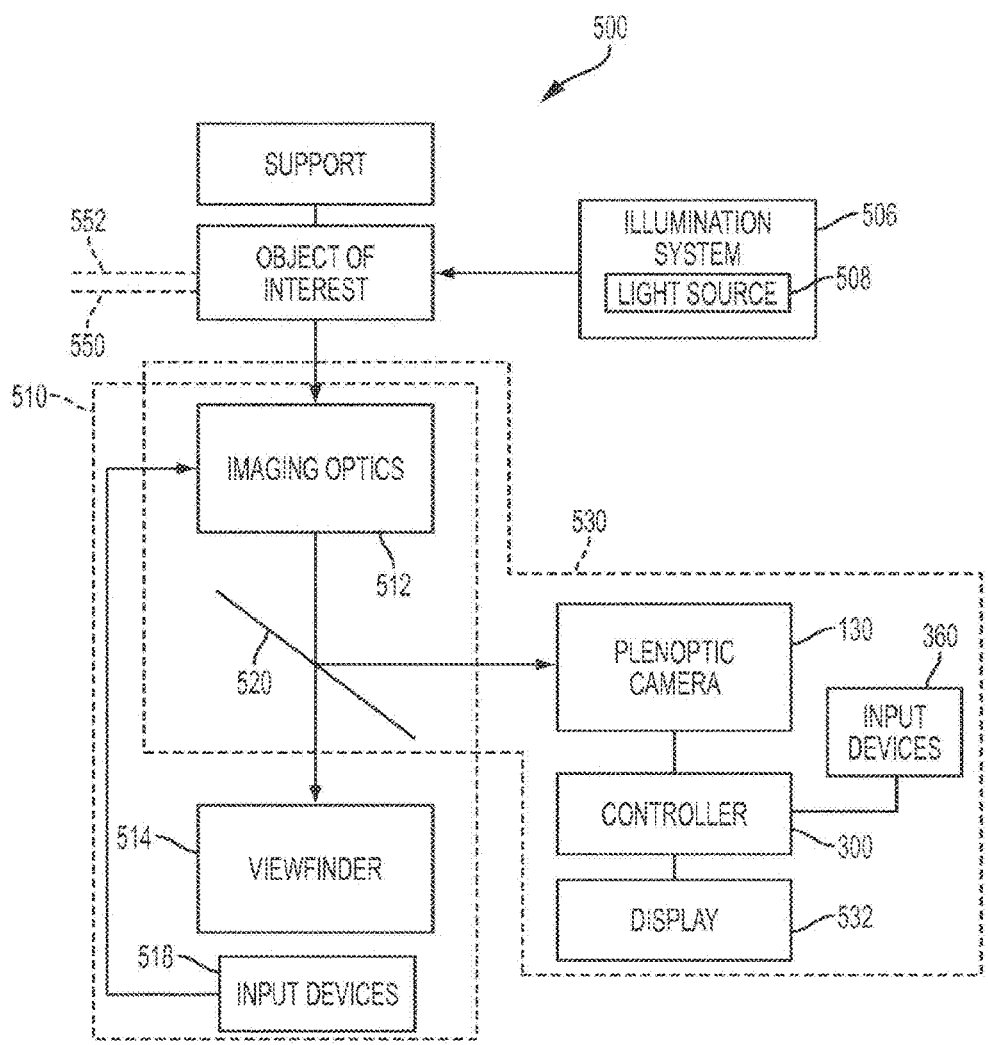
FIG. 25 illustrates an exemplary optical microscope of the present disclosure.

Referring to FIG. 25, an optical microscope 500 is illustrated. Optical microscope 500 is an exemplary imaging system for imaging at least a portion of an object of interest 502. An exemplary object of interest is the eye 10 of a patient. An exemplary optical microscope 500 is an operating microscope used during surgical procedures. Optical microscope 500 includes a support 504 adapted to support the object of interest 502. In the case of the eye 10, an exemplary support may be patient support 206 described herein in connection with FIG. 6. Optical microscope 500 further includes an Illumination system 506 including a light source 508. Illumination system 506 produces light to illuminate the object of interest 502.

Optical microscope further includes an observation system 540 including a first observation unit 510 and a second observation unit 530. First observation unit 510 includes imaging optics 512 configured to receive imaging rays produced by reflection of light from the object of interest 502. The imaging optics 512 provide an image of a desired object plane 550 of the object of interest. First observation unit 510 further includes a viewfinder 514 through which an operator may view the image formed by optics 512. The light travels through a beam splitter 520 to reach viewfinder 514.

As is known in the art, a spacing or other characteristic of optics 512 may be altered to offset the focus of the imaging optics 512 from the desired object plane to an offset object plane 552. This is done to allow the operator of the first observation unit 510 to take into account the optical power of the viewfinder and/or the optical power of the operator's eyes. Thus, the image formed by imaging optics 512 alone will not be of the desired object plane 550, but rather an offset plane 552 from the first object plane to take into account the optical power of the viewfinder 514 and/or operator's eyes. In FIG. 25, input devices 518 are provided to make such adjustments to imaging optics 512. Exemplary input devices include keys, buttons, joysticks, dials, switches, and other devices which control the imaging characteristics of optics 512

Second observation unit 530 shares the imaging optics 512 and beam splitter 520 with first observation unit 510. Second observation system 530 further includes a plenoptic camera 130 which is coupled to a controller 300. Controller 300 displays an image captured by plenoptic camera 130 on a display 532.

A person viewing the image displayed with display 532 may not be satisfied with the focus of the image because it is not focused at the desired object plane 550. As stated earlier, the operator of first observation system 510 has set the characteristics of imaging optics 512 to provide the desired image through view finder 514. This may result in a fuzzy image being displayed with display 532. Through input devices 360 a person viewing the image displayed with display 532 can utilize the light field data recorded by plenoptic camera 130 to provide a refocused image on display 532 which is focused at the desired object plane 550.

In one embodiment, controller 300 includes processing sequences to monitor one or more portions of eye 10 over time. Controller 300 based on the received images determines whether a position of a structure of the eye 10 has changed over time. In one example, controller 300 monitors posterior capsule 30 of eye 10 to determine whether it has moved forward towards the anterior portion of eye 10. This type of movement is important to note when performing surgery on eye 10, such as providing a replacement lens 18 for eye 10. During surgery, an opening is provided in the anterior capsule 31 of eye 10 and the removal of lens 18 is aided with an ultrasonic probe. The posterior capsule 30 may move forward during or subsequent to this process. If the probe contacts the posterior capsule 30, the posterior capsule 30 may be punctured.

Figure 25A:
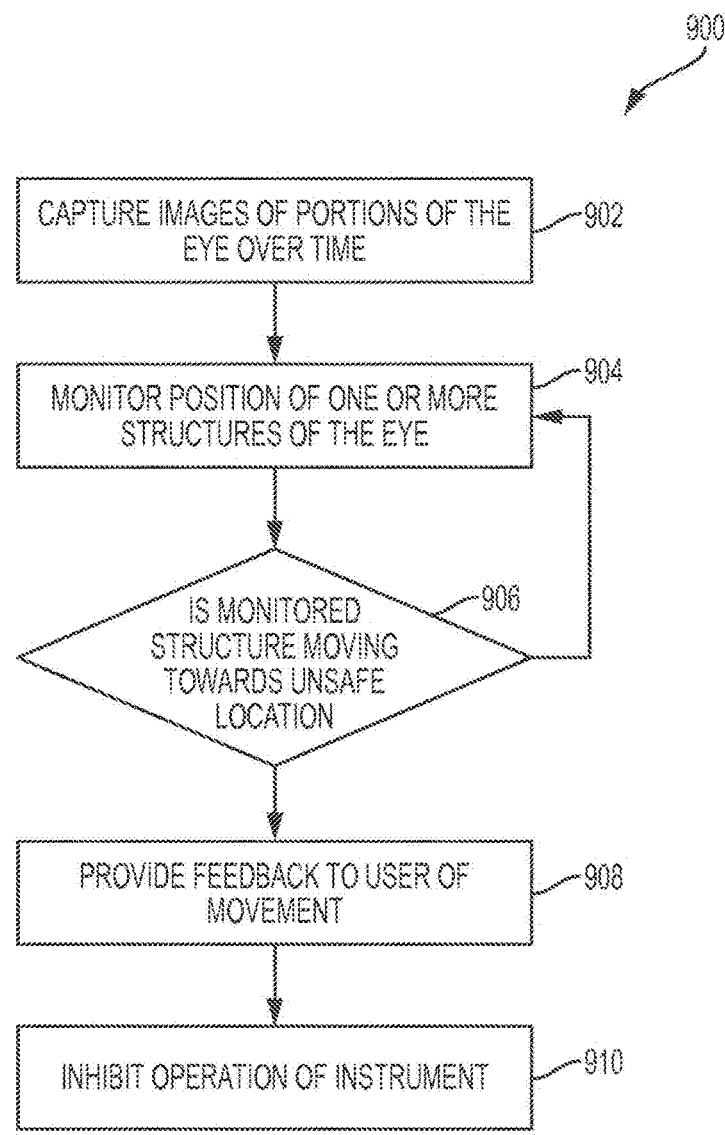
FIG. 25A illustrates an exemplary processing sequence of a controller of the present disclosure.

Referring to FIG. 25A, an exemplary processing sequence 900 is illustrated. Examination system 500 captures images of portions of eye 10 over time, as represented by block 902. Controller 300 analyzes the images to determine the positions of one or more monitored structures of the eye 10, as represented by block 904. An exemplary structure is posterior capsule 30. Since the images are taken with a plenoptic camera 130, controller 300 may utilize the light field data to determine the relative positions of portions of the eye 10 over time including the position of the posterior capsule 30.

Controller 300 determines if the one or more monitored structures are moving towards an unsafe location, as represented by block 906. In the case of the posterior capsule 30, controller 300 determines whether the posterior capsule 30 is moving forward towards the anterior side of the eye 10. In one example, controller 300 determines whether the movement of the monitored structure has exceeded a threshold amount. If not, the controller 300 continues to monitor the position of the one or more monitored structures of the eye 10. If so, controller 300 provides feedback to the operator of the movement of the one or more monitored structures towards an unsafe location, as represented by block 908. Exemplary types of the feedback include one or more of audio, visual, and tactile outputs. Controller 300 may further provide an input to an instrument contacting the eye to inhibit further operation of the instrument, as represented by block 910. In the case of lens removal, the instrument may be an ultrasonic probe and controller 300 may inhibit further operation of the probe based on the location or movement of the posterior capsule 30.

Figure 25B:
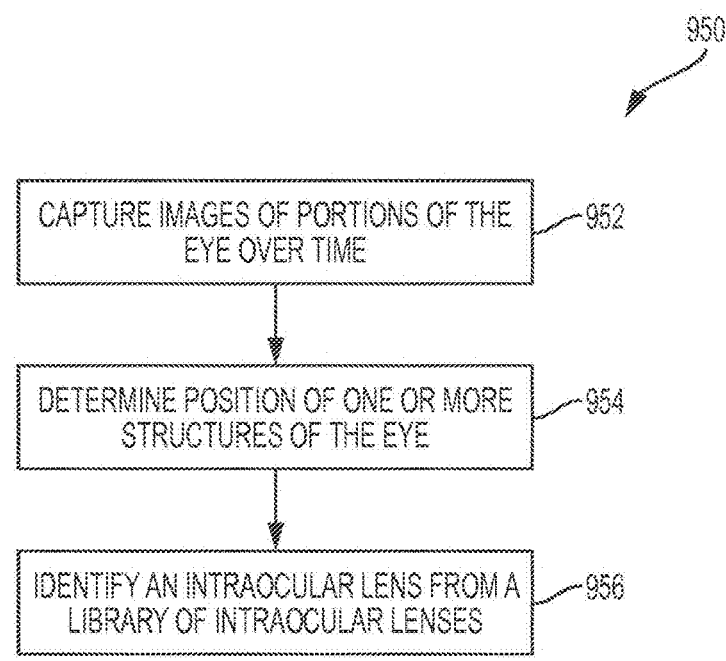
FIG. 25B illustrates an exemplary processing sequence of a controller of the present disclosure.

Referring to FIG. 25B, an exemplary processing sequence 950 of controller 300 is illustrated. Processing sequence 950 assists a user in selecting an appropriate intraocular lens for placement in an eye during cataract surgery. Controller 300 analyzes the images taken with plenoptic camera 130 to determine a position of one or more of the cornea 12, the anterior capsule 31, the posterior capsule 30, the corneal curvature, the position of the suspensory ligaments 34, and the position of the retina 22, as represented by block 952. In one embodiment, camera 130 is focused on a first one of the plurality of anatomical structures and, in order to focus on another one of the plurality of anatomical structures, controller 300 through use of the light field data defocuses the image. Controller 300 then may use the determined change in focus distance of the image to determine the offset distance from the first anatomical structure and thus obtain a measure of the distance between the two anatomical structures.

Based on the determined positions, controller 300 suggests a first intraocular lens from a library of intraocular lens, as represented by block 954. In one embodiment, the first intraocular lens is selected from the library of intraocular lens through a comparison of the determined positions to a database of determined positions for historical patients and a rating of the selected intraocular lens for those respective historical patients.

In one example, after the original lens 18 is removed, the space between the anterior capsule 31 and the posterior capsule 30 is filled with a fluid. Controller 300 then determines a distance between the anterior capsule 31 and the posterior capsule 30. As is known in the art, this distance may be used to select the appropriate replacement lens 18 for insertion into the eye. Controller further determines the position of the suspensory ligaments relative to one of the anterior capsule 31 and posterior capsule 30. Controller 300 then searches a database for empirical data of historical patients having similar separations of the anterior capsule 31 and posterior capsule 30 and similar offsets for the suspensory ligaments 34. The database also includes a measure of the final position of lens 18 after healing for those historical patients. If the final position of lens 18 was as expected then controller 300 suggests a first lens 18. If the final position of lens 18 was different than expected, such as further posteriorly, then controller 300 may suggest a second lens having a different power than the first lens.

Returning the slit-lamp examples provided herein, in addition to standard light-field image processing, the apparatus employs software techniques to collate adjacent images for a specific slit-beam size and angular orientation. A library of adjacent images is created and stored through the techniques described above. This collection of images is analogous to the series of instantaneous slit-lamp images seen by an ophthalmologist scanning across the eye. Separate libraries of images can be created for the slit-views obtained at each slit-beam size and angular orientation. If various slit focal planes are used, separate libraries are created at each position. The images in these libraries can be cross-referenced to similar images in other slit focal planes. These cross-referenced images would be analogous to the images obtained by an ophthalmologist moving the slit-lamp joystick posteriorly so view the tear film, cornea, anterior chamber, iris, lens and vitreous. A different type of cross-referencing can create a library of images analogous to rotating the slit-beam about a pivot point.

These libraries of images allow the end-user to simulate the effect of a slit-lamp examination by using a trackpad, joystick, keyboard, touch-sensitive display screen or similar controller. Depending on the default settings chosen, a given slit image is projected on a display monitor. The user can manipulate the controller (joystick, trackpad, keyboard, touch-sensitive display screen) to simulate an x axis movement of the slit-lamp and call up adjacent x-axis images of the ocular structure of interest. Continued manipulation of the controller in the same direction would cause adjacent images to be displayed on the monitor to create a motion picture similar to the dynamic view obtained by an ophthalmologist using a slit-lamp.

Moving the controller in the y-axis would cause an upper or lower part of the captured image to be displayed. Moving the controller in z-axis would cause a different focal plane to come into focus. These z-axis movements could display a refocused light-field image—or in the case of a thin slit—a new light-field image of the same position but a posteriorly focused thin slit. In this manner, more anterior or posterior portions of the ocular structure would be visualized. Other controllers could call up images with thicker or thinner slit beams to simulate changing the slit thickness on a slit lamp. Likewise, other controllers could call up images with different slit beam orientations to simulate rotating the slit beam apparatus around its pivot point.

The previously described techniques of imaging use light-field photography to image a slit-beam as it illuminates various structures in the eye. In another embodiment of the apparatus, the light-field photography is performed without a slit-beam. Instead diffuse illumination is used, but during the viewing mode software selectively illuminates certain pixels so that a virtual slit effect is obtained. The end user can then use a mouse, joystick, keyboard, trackpad, touch-sensitive screen or similar controller to manipulate the virtual slit to simulate an entire slit-lamp exam. The advantage of this approach would be the elimination of the need for multiple slit-beam passes of the eye structures and the computing power necessary to perform the light-field photography reconstructions. Similarly, instead of illuminating certain pixels, another embodiment of the device uses bright diffuse illumination of the eye structures, and then software selectively dims the brightness of the majority of the image pixels, leaving only those pixels in a virtual slit configuration at the brightest level. Software can selectively create the inverse of this type of image (dimmed slit-beam in a brightly illuminated field) as this may allow for diagnostic views not possible in any conventional slit lamp examination.

The software portion of the apparatus allows for various playback and sharing settings. Comparison of a current examination to previous examinations can be made through side-by-side or overlay display. Slit lamp images can be made available to patients or other professionals either in raw form allowing the user to "drive through" the exam again, or a through a summary video created from the raw data.

One embodiment of the device adapts the plenoptic camera and logic systems described above to be used in conjunction with an operating microscope. This embodiment uses the light-field data and a processor to adjust the z-plane focus in real-time to either a user-defined plane or a plane chosen by an image recognition and tracking system locked on to pertinent eye anatomy such as the surgical limbus, conjunctival vessels or iris aperture. The x and y-axis can also be tracked using this system. Alternatively, the device allows for post-surgical adjustments of the z-axis focal plane and x- and y-axis orientation to allow for less fatiguing viewing of surgical video or for the post-processing of surgical video for educational dissemination.

One embodiment of the device uses a gonioscopic lens attachment to permit ophthalmologic viewing of the filtration angle structures of the eye using the slit-lamp, plenoptic camera and logic systems described above.

One embodiment of the device uses a fundus lens attachment similar to a Hruby lens, 78 diopter, 90 diopter or Volk Superfield lens to permit ophthalmologic viewing of the posterior vitreous and retina using the slit-lamp, plenoptic camera and logic systems described above.

One embodiment of the device uses a Goldmann tonometer attachment to the slit-lamp, plenoptic camera and logic systems described above to facilitate the measurement of the intraocular pressure in the eye.

One embodiment of the device optimizes the optics to examine the structures of the eye through the use of specular reflection. This embodiment allows for qualitative and quantitative evaluation of the corneal endothelium and includes the measurement of the endothelial cell count.

Other embodiments of the device combine the plenoptic imaging system with other established ocular imaging systems including but not limited to ocular coherence tomography, scanning laser ophthalmoscopy, and laser interferometry using the same or different patient support 210, the same or different controller 300, memory 430, processor(s) 450, input devices 360, output devises 362, and remote controller 400.

One embodiment of the device uses a Nd-YAG, argon, excimer, femtosecond or other laser in conjunction with the slit-lamp microscope, plenoptic camera and logic systems described above to treat various eye diseases and conditions either locally or remotely through a networked system.

One embodiment of the device attaches either a dropper system or a spray system to the slit lamp microscope to administer ocular pharmaceuticals such as anesthetics, dyes, dilating or constricting drops to aid in diagnosis or treatment of eye disease.

One embodiment of the device incorporates the controller 400 into an electronic medical records system so that the systems described above can be accessed and controlled from within a given patient's medical record. A still photo, video or sets of images or videos can be identified and separately stored in the electronic medical record file. These images or videos can also be printed or electronically to other providers or patients either from within the electronic record or from controllers 300 or 400.

Referring to FIG. 26, examination system 100 is shown including a light source 600 as part of illumination system 102. Referring to FIG. 27, light source 600 includes a plurality of individual sources 602A-JJ. Although thirty-six light sources 602 are illustrated, light source 600 may include fewer or additional light sources 602. Returning to FIG. 26, light source 600 is operably coupled to controller 300 which controls the optical characteristics of each of light sources 602A-JJ. Controller 300 may increase or reduce in intensity level of one or more of light sources 602A-JJ and/or alter a wavelength characteristic of one or more of light sources 602A-JJ. In one embodiment light sources 602A-JJ are dimmable light sources, such as an LED light sources. In another embodiment light sources 602A-JJ are dimmable light sources, such as LED light sources, that also have selectable wavelength spectrums (color-changing) of the emitted light.

In one embodiment the slit lamp 200 illustrated in FIG. 6 includes light source 600. A user of slit lamp 200 may adjust the optical characteristics of one or more of light sources 602A-JJ through the input devices of slit lamp 200. Controller 300 will receive the requested adjustments and alter the output of the respective light sources 602. In one example, the optical characteristics of light sources 602 are adjusted to selectively illuminate various ocular structures of interest. For example, one or more of light sources 602 may be dimmed or turned off to only illuminate a portion of the eye 10.

In one example, the optical characteristics of light sources 602 are adjusted to increase visibility and minimize artifacts that appear in the images captured by plenoptic camera 130. For example, a glare region 610 is shown in the image of FIG. 8. In one embodiment a user would control slit lamp 200 to reduce the intensity level of one or more of light sources 602 to reduce the amount of light that is incident at the glare region 610 in the image. Thus, the intensity of the glare region 610 is reduced. In one example the controller 300 provides the images of eye 10 on a display, such as the image shown in FIG. 8. A user may then click on a region of the image, such as glare region 610, and request that the intensity level be raised or lowered for that region. Controller 300 then would raise or lower the intensity level of one or more of light sources 602 to raise or reduce the light intensity of the selected region, such as glare region 610.

By having individually controllable light sources 602, light source 600 is able to output customizable illumination patterns for illuminating eye 10. Referring to FIG. 28, one example custom illumination pattern is shown wherein the intensity values are represented in a range of 1 to 10, with 1 being not emitting light and 10 being maximum intensity. As shown in FIG. 28, the intensity value for light sources 602V, 602W, 602BB, and 602CC are set to 1, which corresponds to those light sources being turned off. Further, the intensity values of each of light sources 602O-R, 602V, 602X, 602AA, 602DD, and 602GG-JJ each have an illumination level equal to 5. The remaining sources 602 all have an intensity level set to 8. As such, in the illumination pattern shown in FIG. 28 the illumination of light source 600 is reduced in stepwise fashion in a lower right quadrant of light source 600.

Figure 29:
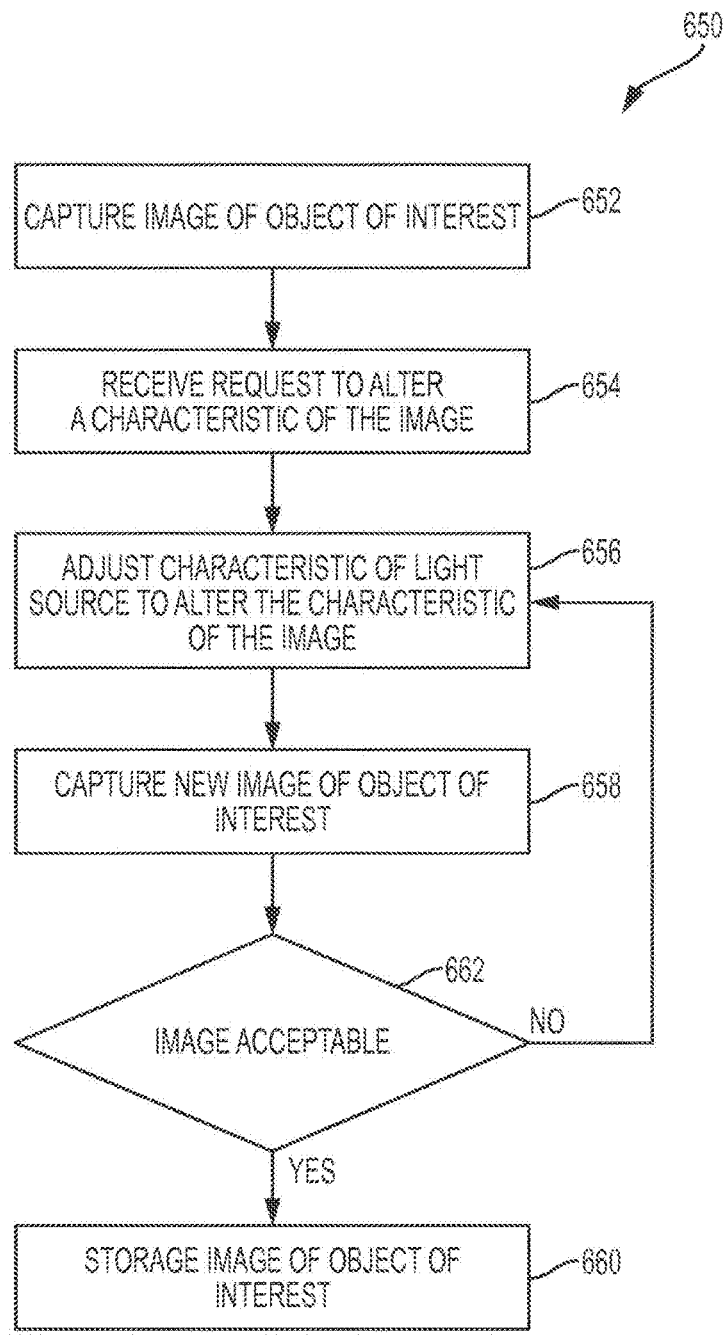
FIG. 29 illustrates an exemplary processing sequence of a controller of the present disclosure.

Referring to FIG. 29, an exemplary processing sequence 650 of controller 300 is shown. The examination system 100 captures an image of the object of interest, illustratively eye 10, with the plenoptic camera 130 as represented by block 652. Controller 300 receives a request to alter a characteristic of the image, as represented by block 654. In one embodiment, controller 300 receives a request through a selection of a portion of the image shown on a display. Controller 300 then adjusts the optical characteristic of one or more light sources 602 to alter the characteristic of the image, as represented by block 656. As explained herein for light source 600, the controller 300 may alter an intensity level of one or more light sources 602 and/or a wavelength spectrum of one or more light sources 602. Controller 300 then captures a new image of the object of interest, as represented by block 658. If the image is considered acceptable, then the image is stored in memory for later retrieval, as represented by block 660. If the image is not acceptable, controller 300 makes further adjustments to the light source 600 to alter the characteristic of the image, as represented by blocks 662 and 656. In one example, controller 300 may lower the intensity level of one or more of light sources 602 in a first iteration and, in response to the image being deemed not acceptable, further lower the intensity level of one or more of light sources 602 in a second iteration. In one example the decision of whether the image is acceptable or not is based upon an input received by controller 300 from the user.

In one embodiment, a characteristic of an image captured by plenoptic camera 130 is altered by controller 300 without modification of a characteristic of the light source of examination system 100. In one example, plenoptic camera 130 is of the type illustrated in FIG. 2B and includes a mask 180 positioned forward of the sensor array 170. Controller 300 includes a processing sequence to remove glare in the captured image. Additional details on computational methods for removing glare from an image are provided in paper titled "Glare Aware Photography: 4D Ray Sampling for Reducing Glare Effects of Camera Lenses," authored by Agrawal et al., SIGGRAPH 2008, http://www.merl.com, Mitsubishi Electric Research Laboratories, the disclosure of which is expressly incorporated by reference herein.

Figure 30:
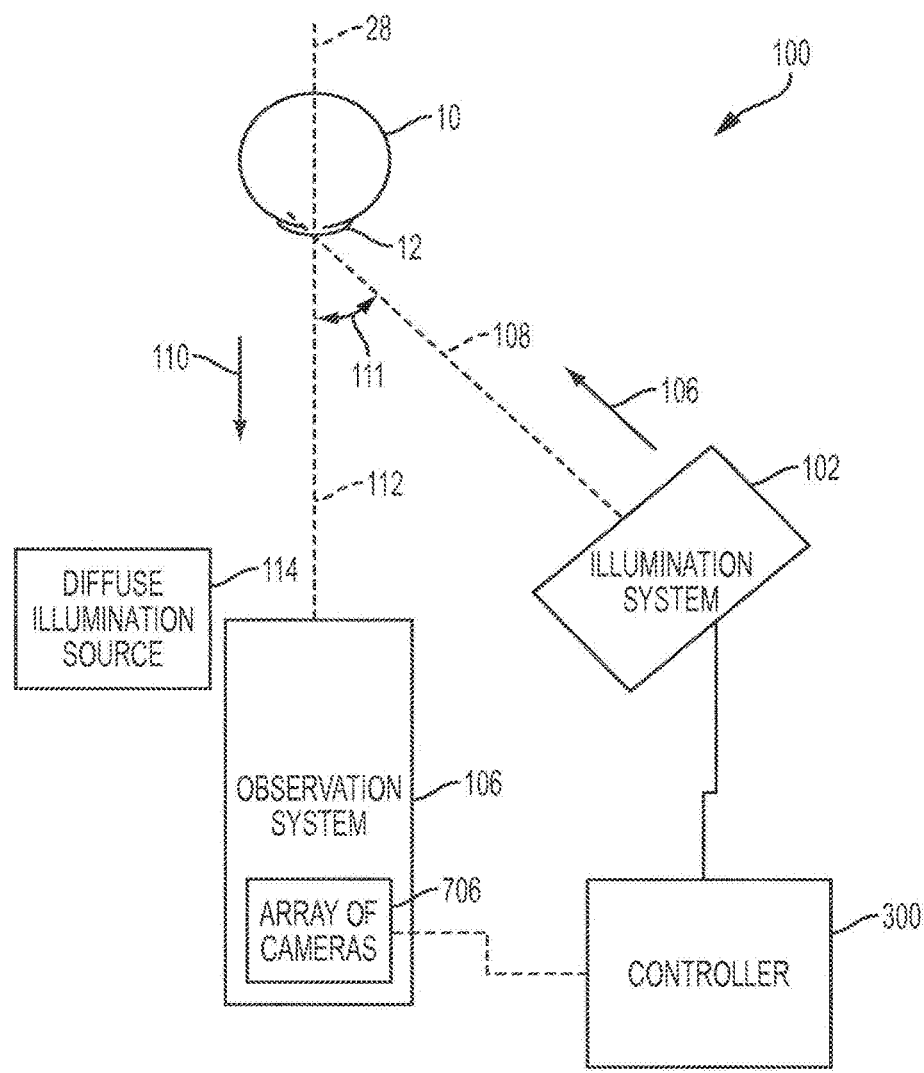
FIG. 30 illustrates an exemplary examination system of the present disclosure.

Referring to FIG. 30, a modified version of examination system 100 is illustrated. As represented in FIG. 30, plenoptic camera 130 is replaced with an array of cameras 706. The cameras which make up the array 706 may be traditional digital cameras or plenoptic cameras, such as plenoptic camera 130. By having an array of cameras, multiple images of eye 10 may be captured simultaneously without moving observation system 106 relative to eye 10. Controller 300 includes exemplary processing sequences to combine information from the images captured by cameras 710 into an image that may be focused at different depths. Exemplary computational methodology is described in paper titled "High Performance Imaging Using Large Camera Arrays," authored by Wilburn et al., ACM Transactions on Graphics (proceedings SIGGRAPH), Vol. 24, No. 3, pp. 765-776, (2005), the entire disclosure of which is expressly incorporated by reference herein.

Figure 31:
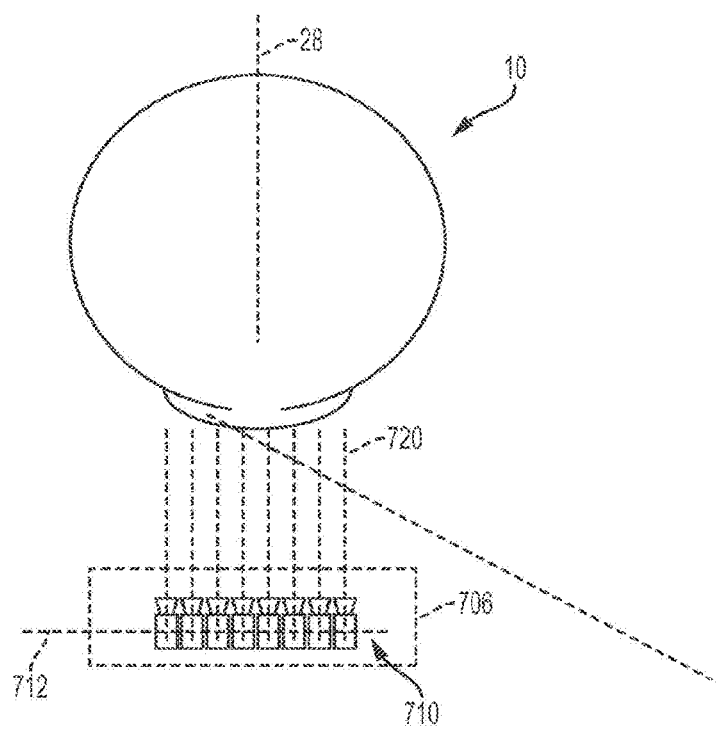
FIG. 31 illustrates an exemplary arrangement of a plurality of cameras of an observation system.

Referring to FIG. 31, in one embodiment array of cameras 706 includes a plurality of cameras 710 arranged in a line 712 generally perpendicular to the optical axis 28 of eye 10. Each camera has an optical axis 720 that is incident on a portion of the eye. In one example, the optical axes 720 are parallel. Each camera 710 may have associated imaging optics to focus the camera on a portion of the eye. Although a one-dimensional array of cameras is illustrated, it is contemplated to have multiple rows of cameras above and below the cameras shown in FIG. 31. By having multiple cameras 710 simultaneously capture images of eye 10 at spaced-apart locations, the scan illustrated in FIG. 12 may be completed in less time. For example, if camera array 706 includes a sufficient number of cameras 710, then the scan illustrated in FIG. 12 may be completed in the time it takes to capture a single image with each camera. As such, no linear movement of the observation system 106 relative to eye 10 in directions 146 or 148 would be required to complete the exemplary scan of FIG. 12.

Figure 32:
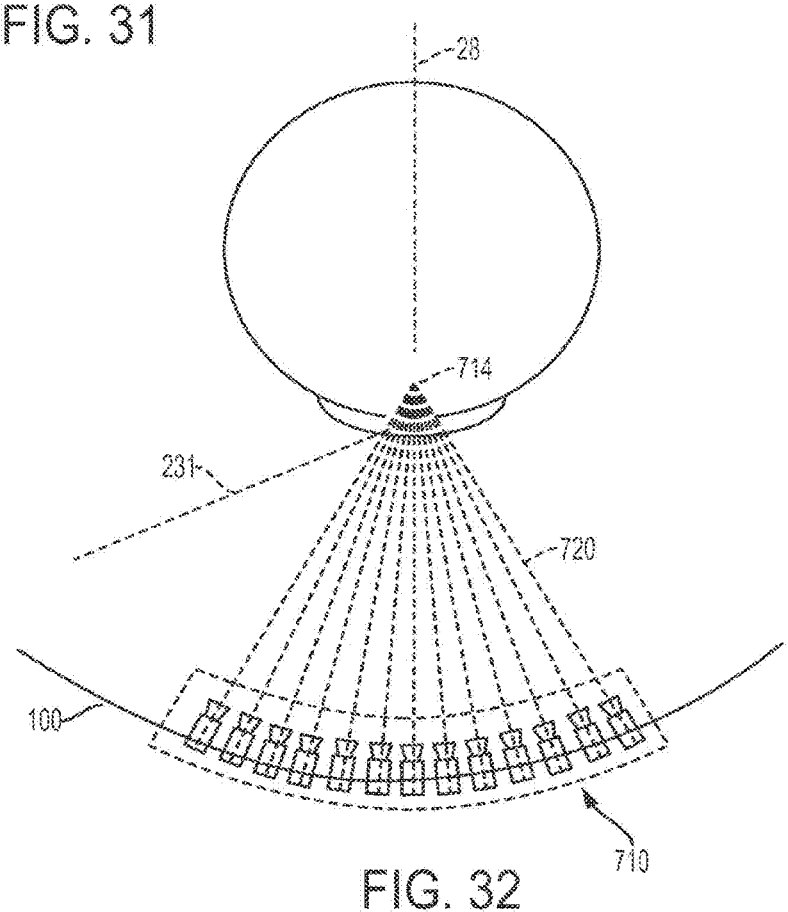
FIG. 32 illustrates another exemplary arrangement of a plurality of cameras of an observation system.

Referring to FIG. 32, another arrangement of cameras 710 and camera array 706 is illustrated. In the arrangement shown in FIG. 32, cameras 710 are angled such that their respective optical axes 712 converge toward a common spot 714 proximate a structure within or near eye 10. Although a one-dimensional array of cameras is illustrated, it is contemplated to have multiple rows of cameras above and below the cameras shown in FIG. 31 with their optical axis also converging towards the common spot 714. As such, assuming a sufficient number of cameras 710, rotational movement of the observation system 106 relative to eye 10 would not be required to complete the exemplary scan of FIG. 13. In one example, the cameras are arranged on an arc. An exemplary arc is a circular arc.

Figure 33:
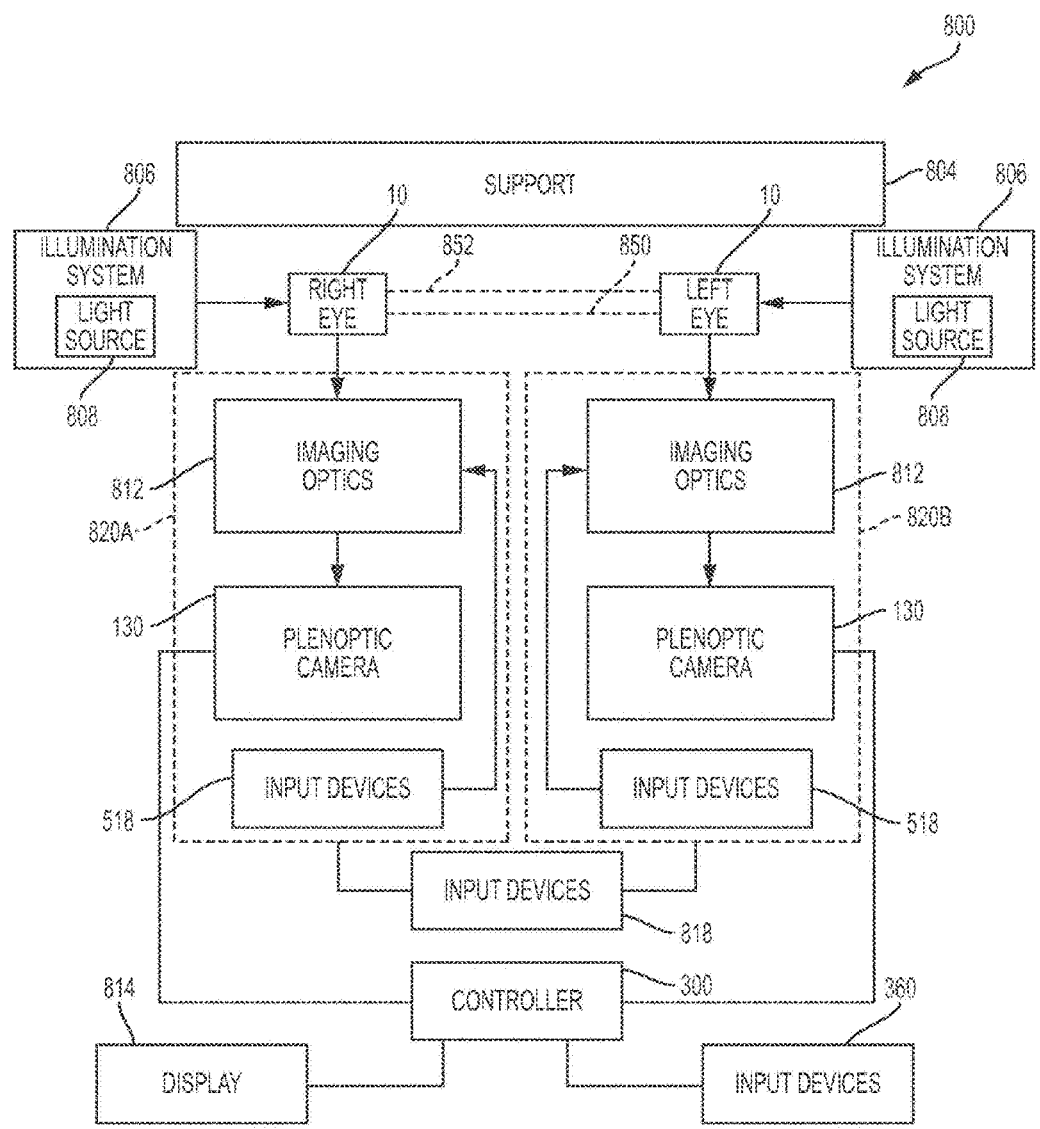
FIG. 33 illustrates an exemplary examination system of the present disclosure.

Referring to FIG. 33, an examination system 800 is shown. Examination system 800 includes a support 804 adapted to support a patient and to position the left and right eyes 10 of the patient. An exemplary support may be patient support 206 described herein in connection with FIG. 6. Examination system 800 further includes two illumination systems 806, each including at least one light source 808. Illumination systems 806 produce light to illuminate the eyes 10 of the patient. In one embodiment a single illumination system is used to illuminate both the left eye 10 and the right eye 10 of the patient.

Examination system 800 further includes two observation systems 820A and 820B. Each of the observation systems 820 includes imaging optics 812 configured to receive imaging rays produced by reflection of the light from the respective eyes 10 of the patient. The respective imaging optics 812 provide an image of a desired object plane 850 of the left and right eye. In particular, observation system 820A images right eye 10 and observation system 820B images left eye 10. The imaging rays passing through imaging optics 812 are provided to respective plenoptic cameras 130, which in turn provide images of the respective eye 10 of the patient to a controller 300. The images are displayed on an associated display 814 by controller 300 for observation by a user. The user may adjust the intrapupillary spacing between observation systems 820A and 820B through input device 818. In one embodiment, both observation systems 820A and 820B are supported on a support, such as moveable base 208 of FIG. 6. Observation systems 820A and 820B are able to move relative to moveable base 208. In one example observations systems 820A and 820B are able to slide relative to move in a linear direction relative to moveable base 208. A turnbuckle is coupled to each of observation systems 820 and turned to alter a spacing between observation systems 820A and 820B. Alternatively, controller 300 may utilize the light-field images provided by respective plenoptic cameras 130 and make adjustments to account for the intrapupillary distance between the eyes.

Examination system 800 allows the user to obtain images of both the left and right eyes 10 of a patient and, subsequent to capturing images, to adjust the depth of focus from object plane 850 to an offset object plane 852 in order to view other structures of the eye. This allows the operator to independently change a depth of focus of both the left and right eye images and view various structures of the respective eyes.

In an exemplary embodiment of the present disclosure, an imaging system for imaging at least a portion of an eye of a patient is provided. The system comprising a patient support adapted to position the eye of the patient; a movable base moveable relative to the patient support; and an illumination system. The illumination system including at least one light source producing light to illuminate the eye and an illumination system support arm supporting the light source. The illumination system support arm being supported by the moveable base and rotatable relative to the moveable base. The system further comprising an observation system including a plenoptic camera configured to receive imaging rays produced by reflection of light from the eye, and an observation system support arm supporting the imaging system. The observation system support arm being supported by the moveable base and rotatable relative to the moveable base. The observation system further comprising a storage device operatively coupled to the plenoptic camera to receive and store a plurality of images of the eye imaged by the plenoptic camera, each of the stored images having at least one associated component characteristic of one of the patient support, the movable base, the illumination system, and the observation system. In one example, the illumination system further includes a slit forming device which receives illuminating light produced by the at least one light source and provides a line of light to illuminate the eye, the illumination system support arm supporting the slit forming device and wherein the plenoptic camera receives imaging rays produced by reflection of the line of light from the eye. In another example, the illumination system includes a plurality of light sources arranged in an array, the plurality of light sources each produce light to illuminate the eye. In a variation thereof, an illumination characteristic of a portion of the plurality of light sources is adjusted through an input device. In a refinement thereof, the illumination characteristic is one of an intensity level and a wavelength spectrum. In another variation thereof, an illumination characteristic of a portion of the plurality of light sources is adjusted through an electronic controller. In a refinement thereof, the illumination characteristic is one of an intensity level and a wavelength spectrum. In a further example, the observation system support arm is rotatable relative to the moveable base independent of the illumination system support arm. In yet a further example, the illumination system support arm is rotatable relative to the moveable base about a first rotation axis and the observation system support arm is rotatable relative to the moveable base about the first rotation axis.

In another exemplary embodiment, a method of analyzing an eye of a patient which has been illuminated with a slit-lamp microscope is provided. The slit-lamp microscope including an illumination system and an observation system. The illumination system including a light source and a slit forming device which provides a line of light to illuminate the eye and the observation system including an imaging system including a plenoptic camera configured to receive imaging rays produced by reflection of the line of light from the eye. The method comprising the steps of storing a plurality of images of the eye imaged by the plenoptic camera while the eye was illuminated with the line of light, each of the stored images having at least one associated slit-lamp microscope characteristic; receiving an image request; and providing a requested image based on at least one of the plurality of images, the image request, and the at least one associated slit-lamp microscope characteristic of the at least one of the plurality of images. In one example, the requested image includes the line of light focused on a first portion of a curved structure. In another example, the method further comprises the steps of receiving an image request for a second image having the line of light focused on a second portion of the curved structure, wherein the line of light is displaced in at least one of an x-axis direction and a y-axis direction and in a z-axis direction; and generating the second image from at least one of the stored images and the light field data of the at least one stored image. In a further example, the method further comprises the step of requesting to walk through the stored images sequentially. In yet a further example, the method further comprises the steps of retrieving an image set from a prior examination; and identifying an image from the prior examination having the same associated slit-lamp microscope characteristic as the requested image. In yet a further example, the associated slit-lamp microscope characteristic is one or more of an x-axis position of a moveable base of the slit-lamp supporting the illumination system and the observation system, a y-axis position of the moveable base, a z-axis position of the moveable base, a rotational position of the illumination system, a rotational position of the observation system, a slit width of the slit-forming device, and a magnification of the observation system. In still yet another example, the method further comprises the steps of receiving an image request for a second image having the line of light focused on at a different depth within the eye than the first image; and generating the second image from at least one of the stored images and the light field data of the at least one stored image.

In yet another exemplary embodiment of the present disclosure, an imaging system for imaging at least a portion of an eye of a patient is provided. The system comprising a patient support adapted to position the eye of the patient; an illumination system including a light source producing light to illuminate the eye; and an observation system including a plurality of cameras in a spaced apart arrangement, each camera positioned to receive imaging rays produced by reflection of light from the eye. In one example, each camera has an optical axis and the plurality of optical axes are parallel. In another example, the plurality of cameras are arranged along a line generally perpendicular to the optical axes of the plurality of cameras. In a further example, each camera has an optical axis and the plurality of optical axes converge towards a common point. In a variation thereof, the plurality of cameras are arranged along an arc. In a refinement thereof, the arc is a circular arc and the common point is a center of the circular arc. In still another example, the plurality of cameras are plenoptic cameras.

In a further exemplary embodiment of the present disclosure, a method of analyzing an eye of a patient is provided. The method comprising the steps of illuminating the eye with an illumination system, the illumination system including a light source and a slit forming device which provides a line of light to illuminate the eye; positioning a first camera relative to the eye to receive imaging rays produced by a reflection of the line of light from the eye; positioning a second camera relative to the eye to receive imaging rays produced by the reflection of the line of the light from the eye; and storing a plurality of images of the eye imaged by the first camera and the second camera while the eye was illuminated with the line of light. In one example, each of the first camera and the second camera have an optical axis which are parallel to each other. In a variation thereof, the first camera and the second camera are arranged along a line generally perpendicular to the optical axes of the first camera and the second camera. In another example, each of the first camera and the second camera have an optical axis that converge towards a common point. In another variation thereof, the first camera and the second camera are arranged along an arc. In a refinement thereof, the arc is a circular arc and the common point is a center of the circular arc. In a further refinement thereof, the plurality of cameras are plenoptic cameras.

In yet a further exemplary embodiment of the present disclosure, an imaging system for imaging at least a portion of an eye of a patient is provided. The system comprising a patient support adapted to position the eye of the patient; an illumination system including a light source producing light to illuminate the eye; and an observation system including imaging optics configured to receive imaging rays produced by reflection of light from the eye which are focused by the imaging optics at a first object plane, a first observation unit including a viewfinder which receives imaging rays from the imaging optics and a second observation unit which receives the imaging rays from the imaging optics, the second observation unit including a plenoptic camera and a display, the second observation unit displaying an image of the eye generated based on the imaging rays, the image of the eye being focused at a second object plane spaced apart from the first object plane. In one example, the imaging system further comprises a beamsplitter, the imaging rays reaching the viewfinder through a first path through the beamsplitter and reaching the plenoptic camera through a second path through the beamsplitter. In another example, the first object plane is offset from the second object plane. In a further example, the illumination system includes a plurality of light sources arranged in an array, the plurality of light sources each produce light to illuminate the eye. In a variation thereof, an illumination characteristic of a portion of the plurality of light sources is adjusted through an input device. In a refinement thereof, the illumination characteristic is one of an intensity level and a wavelength spectrum.

In yet still another exemplary embodiment of the present disclosure, a method of analyzing an eye of a patient is provided. The method comprising the steps of illuminating the eye with an illumination system; receiving with imaging optics imaging rays produced by reflection of light from the eye; directing the imaging rays to a viewfinder; directing the imaging ray to a plenoptic camera; focusing the imaging optics on a first object plane in the eye; and displaying on a display operatively coupled to the plenoptic camera a second object plane in the eye. In one example, the first object plane is offset from the second object plane. In a variation thereof, the first object plane take into account at least one of an optical power of the viewfinder and the optical power of an operator's eyes such that the resultant image viewed by the operator through the viewfinder is focused at the second object plane.

In still a further exemplary embodiment of the present disclosure, an imaging system for imaging at least a portion of a left eye of a patient and at least a portion of a right eye of the patient is provided. The system comprising a patient support adapted to position the left eye and the right eye of the patient; at least one illumination system including at least one light source producing light to illuminate the left eye and the right eye; a first observation system including a first plenoptic camera configured to receive imaging rays produced by reflection of light from the left eye; a second observation system including a second plenoptic camera configured to receive imaging rays produced by reflection of light from the right eye; and a storage device operatively coupled to the first plenoptic camera and to the second plenoptic camera to receive and store a plurality of images of the eye imaged by the first plenoptic camera and the second plenoptic camera. In one example, the at least one illumination system includes a first illumination system including at least a first light source producing light to illuminate the left eye and a second illumination system including at least a second light source producing light to illuminate the right eye.

In a further exemplary embodiment of the present disclosure, a method of analyzing an eye of a patient with an imaging system including an illumination system and an observation system is provided. The illumination system includes a light source. The observation system including an imaging system including a camera configured to receive imaging rays produced by reflection of light from the eye. The method comprising the steps of capturing images of a portion of the eye over time with the camera; monitoring a position of a structure of the eye in the captured images; determining if the structure of the eye is moving towards an unsafe location; and if the structure is moving towards an unsafe location, providing feedback of such movement. In one example, the method further comprises the step of providing a signal to inhibit operation of an instrument which is used to alter a portion of the eye. In a variation thereof, the instrument is an ultrasound probe. In another example, the step providing feedback of such movement includes at least one of providing an audio output, providing a visual output, and providing a tactile output. In a further example, the camera is a plenoptic camera. In a variation thereof, the structure is a posterior capsule of the eye and the step of determining if the structure of the eye is moving towards the unsafe location includes the step of determining if the posterior capsule is moving forward towards the anterior side of the eye. In a refinement thereof, the step of determining if the structure of the eye is moving towards the unsafe location includes the step of determining whether the movement of the structure has exceeded a threshold amount. In yet a further example, the step of determining if the structure of the eye is moving towards the unsafe location includes the step of determining whether the movement of the structure has exceeded a threshold amount.

In a yet further exemplary embodiment of the present disclosure, a method of analyzing an eye of a patient with an imaging system including an illumination system and an observation system is provided. The illumination system includes a light source. The observation system including a camera configured to receive imaging rays produced by reflection of light from the eye. The method comprising the steps of capturing images of a portion of the eye over time with a plenoptic camera; determining positions of one of more structures of the eye from the captured images; and identifying a first intraocular lens from a library of intraocular lenses for placement in the eye based on the determined positions. In one example, the step of identifying the first intraocular lens from the library of intraocular lenses for placement in the eye based on the determined positions includes the step of comparing the determined positions of the one or more structures of the eye with a database of determined positions for historical patients and a rating of the selected intraocular lens for the historical patients. In a variation thereof, the determined positions includes a distance between an anterior capsule of the eye and an posterior capsule of the eye and a position of suspensory ligaments of the eye relative to one of the anterior capsule and the posterior capsule. In a refinement thereof, the database also includes a measure of the final position of a replacement lens of the historical patients and the step of identifying a first intraocular lens identifies the a first lens if the measure has a first value indicating the final position of the lens for a historical patient was as expected and a second lens if the measure has a second value indicating that the final position of the lens for the historical patient was different than expected, the second lens having a different optical power than the first lens.

In still another exemplary embodiment of the present disclosure, an imaging system for imaging at least a portion of an eye of a patient is provided. The system comprising a patient support adapted to position the eye of the patient; an illumination system including a plurality of light sources, each producing light to illuminate the eye; and an observation system including imaging optics configured to receive imaging rays produced by reflection of light from the eye. In one example, the observation system includes a plenoptic camera which receives the imaging rays from the imaging optics. In a variation thereof, the imaging system further comprises a storage device operatively coupled to the plenoptic camera to receive and store a plurality of images of the eye imaged by the plenoptic camera, each of the stored images having at least one associated component characteristic of one of the illumination system and the observation system. In another example, the illumination system further includes a slit forming device which receives illuminating light produced by the at least one light source and provides a line of light to illuminate the eye and wherein the plenoptic camera receives imaging rays produced by reflection of the line of light from the eye. In still another example, the plurality of light sources are arranged in an array. In a variation thereof, an illumination characteristic of a portion of the plurality of light sources is adjusted through an input device. In a refinement thereof, the illumination characteristic is one of an intensity level and a wavelength spectrum. In another variation, an illumination characteristic of a portion of the plurality of light sources is adjusted through an electronic controller. In a refinement thereof, the illumination characteristic is one of an intensity level and a wavelength spectrum.

In still another exemplary embodiment of the present disclosure, a method of analyzing an eye of a patient is provided. The method comprising the steps of illuminating the eye with an illumination system, the illumination system including a plurality of light sources; receiving with imaging optics imaging rays produced by reflection of light from the eye; directing the imaging rays to a camera to capture an image; displaying the image; and adjusting an illumination characteristic of a portion of the plurality of light sources to alter an illumination of a portion of the eye. In one example, the illumination characteristic is one of an intensity level and a wavelength spectrum. In another example, the illumination characteristic is adjusted to reduce glare at the portion of the eye.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An imaging system for imaging at least a portion of an eye of a patient, the system comprising:
    a patient support adapted to position the eye of the patient;
    a movable base moveable relative to the patient support;
    an illumination system including at least one light source producing light to illuminate the eye and an illumination system support arm supporting the light source, the illumination system support arm being supported by the moveable base and rotatable relative to the moveable base;
    an observation system including a plenoptic camera configured to receive imaging rays produced by reflection of light from the eye, and an observation system support arm supporting the imaging system, the observation system support arm being supported by the moveable base and rotatable relative to the moveable base; and
    a storage device operatively coupled to the plenoptic camera to receive and store a plurality of images of the eye imaged by the plenoptic camera, each of the stored images having at least one associated component characteristic of one of the patient support, the movable base, the illumination system, and the observation system.

2. The imaging system of claim 1, wherein the illumination system further includes a slit forming device which receives illuminating light produced by the at least one light source and provides a line of light to illuminate the eye, the illumination system support arm supporting the slit forming device and wherein the plenoptic camera receives imaging rays produced by reflection of the line of light from the eye.

3. The imaging system of claim 1, wherein the illumination system includes a plurality of light sources arranged in an array, the plurality of light sources each produce light to illuminate the eye.

4. The imaging system of claim 3, wherein an illumination characteristic of a portion of the plurality of light sources is adjusted through an input device.

5. The imaging system of claim 4, wherein the illumination characteristic is one of an intensity level and a wavelength spectrum.

6. The imaging system of claim 3, wherein an illumination characteristic of a portion of the plurality of light sources is adjusted through an electronic controller.

7. The imaging system of claim 6, wherein the illumination characteristic is one of an intensity level and a wavelength spectrum.

8. The imaging system of claim 1, wherein the observation system support arm is rotatable relative to the moveable base independent of the illumination system support arm.

9. The imaging system of claim 1, wherein the illumination system support arm is rotatable relative to the moveable base about a first rotation axis and the observation system support arm is rotatable relative to the moveable base about the first rotation axis.

10. An imaging system for imaging at least a portion of an eye of a patient, the system comprising:
    a patient support adapted to position the eye of the patient;
    an illumination system including a light source producing light to illuminate the eye;
    an observation system including imaging optics configured to receive imaging rays produced by reflection of light from the eye which are focused by the imaging optics at a first object plane, a first observation unit including a viewfinder which receives imaging rays from the imaging optics and a second observation unit which receives the imaging rays from the imaging optics, the second observation unit including a plenoptic camera and a display, the second observation unit displaying an image of the eye generated based on the imaging rays, the image of the eye being focused at a second object plane spaced apart from the first object plane.

11. The imaging system of claim 10, further comprising a beamsplitter, the imaging rays reaching the viewfinder through a first path through the beamsplitter and reaching the plenoptic camera through a second path through the beamsplitter.

12. The imaging system of claim 10, wherein the first object plane is offset from the second object plane.

13. The imaging system of claim 10, wherein the illumination system includes a plurality of light sources arranged in an array, the plurality of light sources each produce light to illuminate the eye.

14. The imaging system of claim 13, wherein an illumination characteristic of a portion of the plurality of light sources is adjusted through an input device.

15. The imaging system of claim 14, wherein the illumination characteristic is one of an intensity level and a wavelength spectrum.

16. An imaging system for imaging at least a portion of a left eye of a patient and at least a portion of a right eye of the patient, the system comprising:
  a patient support adapted to position the left eye and the right eye of the patient;
  at least one illumination system including at least one light source producing light to illuminate the left eye and the right eye;
  a first observation system including a first plenoptic camera configured to receive imaging rays produced by reflection of light from the left eye;
  a second observation system including a second plenoptic camera configured to receive imaging rays produced by reflection of light from the right eye; and
  a storage device operatively coupled to the first plenoptic camera and to the second plenoptic camera to receive and store a plurality of images of the eye imaged by the first plenoptic camera and the second plenoptic camera.

17. The imaging system of 16, wherein the at least one illumination system includes a first illumination system including at least a first light source producing light to illuminate the left eye and a second illumination system including at least a second light source producing light to illuminate the right eye.

* * * * *